US008554493B2

(12) United States Patent
Metcalf et al.

(10) Patent No.: US 8,554,493 B2
(45) Date of Patent: Oct. 8, 2013

(54) VIRAL POLYHEDRA COMPLEXES AND METHODS OF USE

(75) Inventors: Peter Metcalf, Auckland (NZ); Fasseli Joseph Coulibaly, Auckland (NZ); Hajime Mori, Kyoto (JP); Norio Hamada, Ibaraki (JP); Keiko Ikeda, Kyoto (JP); Yui Lam Elaine Chiu, Auckland (NZ); Hiroshi Ijiri, Kameoka (JP)

(73) Assignees: National University Corporation Kyoto Institute of Technology, Kyoto (JP); Protein Crystal Corporation, Kyoto (JP)

( * ) Notice: Subject to any disclaimer, the term of this patent is extended or adjusted under 35 U.S.C. 154(b) by 621 days.

(21) Appl. No.: 12/529,110

(22) PCT Filed: Feb. 28, 2008

(86) PCT No.: PCT/NZ2008/000030

§ 371 (c)(1), (2), (4) Date: Mar. 5, 2010

(87) PCT Pub. No.: WO2008/105672

PCT Pub. Date: Sep. 4, 2008

(65) Prior Publication Data

US 2010/0216651 A1 Aug. 26, 2010

(30) Foreign Application Priority Data

Feb. 28, 2007 (NZ) ........................................ 553519

(51) Int. Cl.
*G06F 19/00* (2011.01)

(52) U.S. Cl.
USPC .................................. 702/27; 703/11; 703/12

(58) Field of Classification Search
None
See application file for complete search history.

(56) References Cited

PUBLICATIONS

J. H. Chang et al.; "An improved baculovirus insecticide producing occlusion bodies that contain Bacillus thuringiensis insect toxin"; Journal Invertebrate Pathologly, vol. 84, No. 1, pp. 30-37, (2003).

R. W. Glaser et al.; "The Nature of the Polyhedral Bodies found in Insects"; Cells Biol. Bull. vol. 30, pp. 367-390 (1916).

G. F. Rohrmann; "Polyhedrin Structure"; J. Gen. Virol., vol. 67, (Pt 8), pp. 1499-1513, (1986).

Christian Riekel et al.; "Protein crystallography microdiffraction"; Current Opinion in Structural Biology, vol. 15, No. 5, pp. 556-562, (2005).

Trevor Douglas et al.; "Viruses: Making Friends with Old Foes"; Science, vol. 312, No. 5775, pp. 873-875, (2006).

Keiko Ikeda et al.; "Immobilization of diverse foreign proteins in viral polyhedra and potential application for protein microarrays"; Proteomics, vol. 6, No. 1, pp. 54-66, (2006).

H. Zhang et al.; "Visualization of Protein-RNA Interactions in Cytoplasmic Polyhedrosis Virus"; Journal of Virology, vol. 73, No. 2, pp. 1624-1629, (1999).

Claire L. Hill et at.; "The structure of a cypovirus and the functional organization of dsRNA viruses"; Nature Structural Biology, vol. 6, No. 6, pp. 565-568, (1999).

R. E. Thorne et al.; "Microfabricated mounts for high-throughput macromolecular cryocrystallography"; J. Appl. Crystallography, vol. 36, No. 6, pp. 1455-1460, (2003).

Johnathan P.K. Doye et al.; "Protein Crystallization in vivo"; Current Opinion in Colloid Interface Science, vol. 11, pp. 40-46, (2006).

Jonathan Grimes et al; "The crystal structure of bluetongue virus VP7"; Nature, vol. 373, pp. 167-170, Jan. 1995.

Susanne Liemann et al.; "Structure of the Reovirus Membrane-Penetration Protein, Mu1, in a Complex with Its Protector Protein, Sigma3"; Cell, vol. 108, pp. 263-295, Jan. 2002.

Fassell Coulibaly et al.; "The Birnavirus Crystal Structure Reveals Structural Relationships among Icosahedral Viruses"; Cell, vol. 120, No. 6, pp. 761-772, Mar. 2005.

Michael C. Lawrence et al.; "Shape Complementarity at Protein/Protein Interfaces"; J. Mol. Biol., vol. 234, No. 4, pp. 946-950, (1993).

Takaji Fujiwara et al.; "X-Ray Diffraction Studies of Polyhedral Inclusion Bodies of Nuclear and Cytoplasmic Polyhedrosis Viruses"; Appl. Entomol. Zool., vol. 19, pp. 402-403, (1984).

(Continued)

*Primary Examiner* — Eric S Dejong
(74) *Attorney, Agent, or Firm* — Westerman, Hattori, Daniels & Adrian, LLP

(57) ABSTRACT

Cypoviruses and baculoviruses are notoriously difficult to eradicate because the virus particles are embedded in micron-sized protein crystals called polyhedra. The remarkable stability of polyhedra means that like bacterial spores these insect viruses remain infectious for years in soil. Although these unique in vivo protein crystals have been extensively characterized since the early 1900s, their atomic organization remains elusive. Here we describe the 2 crystal structure of both recombinant and infectious silkworm cypovirus polyhedra determined using 5-12 micron crystals purified from insect cells. These are the smallest crystals yet used for de novo X-ray protein structure determination. It was found that polyhedra are made of trimers of the viral polyhedrin protein and contain nucleotides. Although the shape of these building blocks is reminiscent of some capsid trimers, polyhedrin has a new fold and has evolved to assemble in vivo into 3-D cubic crystals rather than icosahedral shells. The polyhedrin trimers are extensively cross-linked in polyhedra by non-covalent interactions and pack with an exquisite molecular complementarity similar to that of antigen-antibody complexes. The resulting ultra-stable and sealed crystals shield the virus particles from environmental damage. The structure suggests that polyhedra can serve as the basis for the development of robust and versatile nanoparticles for biotechnological applications such as in cell culture systems, microarrays and biopesticides.

17 Claims, 15 Drawing Sheets

(56) References Cited

PUBLICATIONS

Serge Belloncik et al.; "Cypoviruses"; The Insect Viruses (eds Miller, L. K. and Ball, L. A.), pp. 337-369 (Plenum Publishing Corporation, New York, 1998).
Lois K. Miller; "Introduction to the Baculoviruses"; The Baculoviruses. ( Plenum Publishing Corporation, New York, 1997).
Karin Anduleit et al.; "Crystal lattice as biological phenotype for insert viruses"; Protein Science, vol. 14, No. 10, pp. 2741-2743, (2005).
Hajime Mori et al.; "Expression of Bombyx mori cycoplasmic polyhedrosis virus polyhedrin in insect cells by using a baculovirus expression vector, and its assembly into polyhedra"; Journal of General Virology, vol. 74, No. 1, pp. 99-102, (1993).
Thomas R. Schneider et al.; "Substructure solution with SHELXD"; Biological Crystallography, D58 (10 Part 2), pp. 1772-1779, (2002).
Garib N. Murshudov et al.; "Refinement of Macromolecular Structures by the Maximum-Likelihood Method"; Acta Cryst., D53, (3), pp. 240-255, (1997).
Simon C. Lovell et al.; "Structure validation by Calpha geometry: phi, psi and Cbeta Deviation"; Proteins, vol. 50, No. 3, pp. 437-450, (2003).
Collaborative Computational Project, No. 4; "The CCPA suite: Programs for Protein Crystallography", Acta Cryst. D50, (5), pp. 760-763, (1994).
Evgeny Krissinel et al.; "Detection of Protein Assemblies in Crystals"; Lecture Notes in Computer Science (eds Berthold, M. R.), 3695, pp. 163-174 ( Springer, Berlin Heidelberg, 2005).
Gerard J. Kleywegt et al.; "Detection, Delineation, Measurement and Display of Cavities in Macromolecular Structures"; Acta Cryst., D50, (2), pp. 178-185, (1994).
Daijiro Ohmori et al.; "Characterization and Reconstitution of *Pseudomonas* Ovalis Ferredoxin"; Biochimica et Biophysica Acta, vol. 794, pp. 15-21, (1984).
Showbu Sato et al.; "Purification, Some Properties and Amido Acid Sequence of Thermus Thermophilus HB8 Ferredoxin"; Biochimica et Biophysica Acta, vol. 668, pp. 277-289, (1981).
Gregory T. Drummond et al.; "Electrochemical DNA sensors"; Nature Biotechnology, vol. 21, No. 10, pp. 1192-1199, Oct. 2003.
Heng Zhu et al.; "Protein chip technology", Current Opinion in Chemical Biology vol. 7, pp. 55-63, (2003).
Julia D. Wulfkuhle et al.; "Proteomic Applications for the Early Detection of Cancer"; Nature Reviews Cancer vol. 3, pp. 267-272, (2003).
Radhakrishna S. Tirumalai et al.; "Characterization of the Low Molecular Weight Human Serum Proteome"; Molecular & Cellular Proteomics 2.10, pp. 1096-1103, (2003).
Keiko Ikeda et al.; "Molecular Characterization of Bombyx mori Cytoplasmic Polyhedrosis Virus Genome Segment 4"; J. Virol., vol. 75, pp. 988-995, (2001).

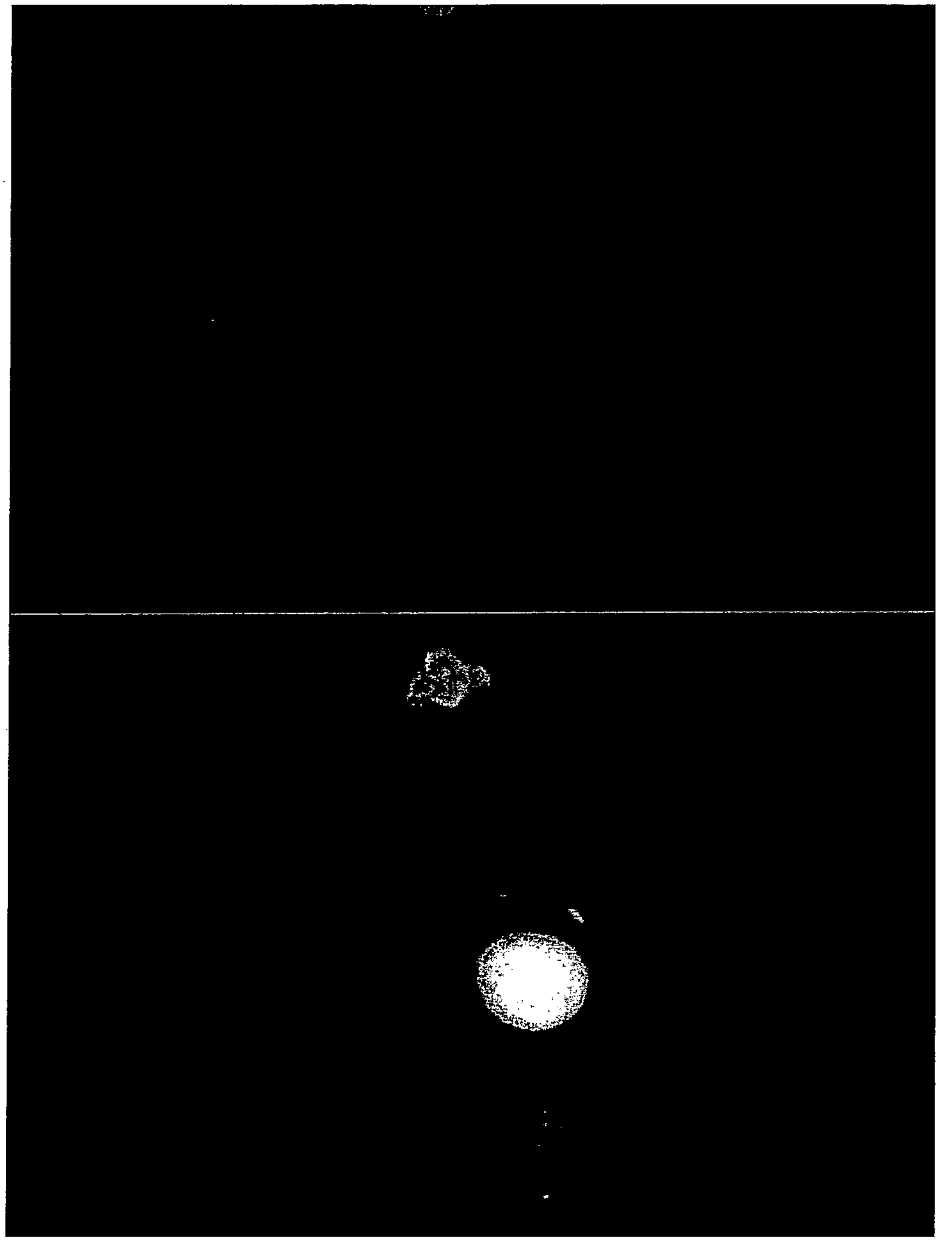
Figure 7A. H1 derived occlusion of GFP

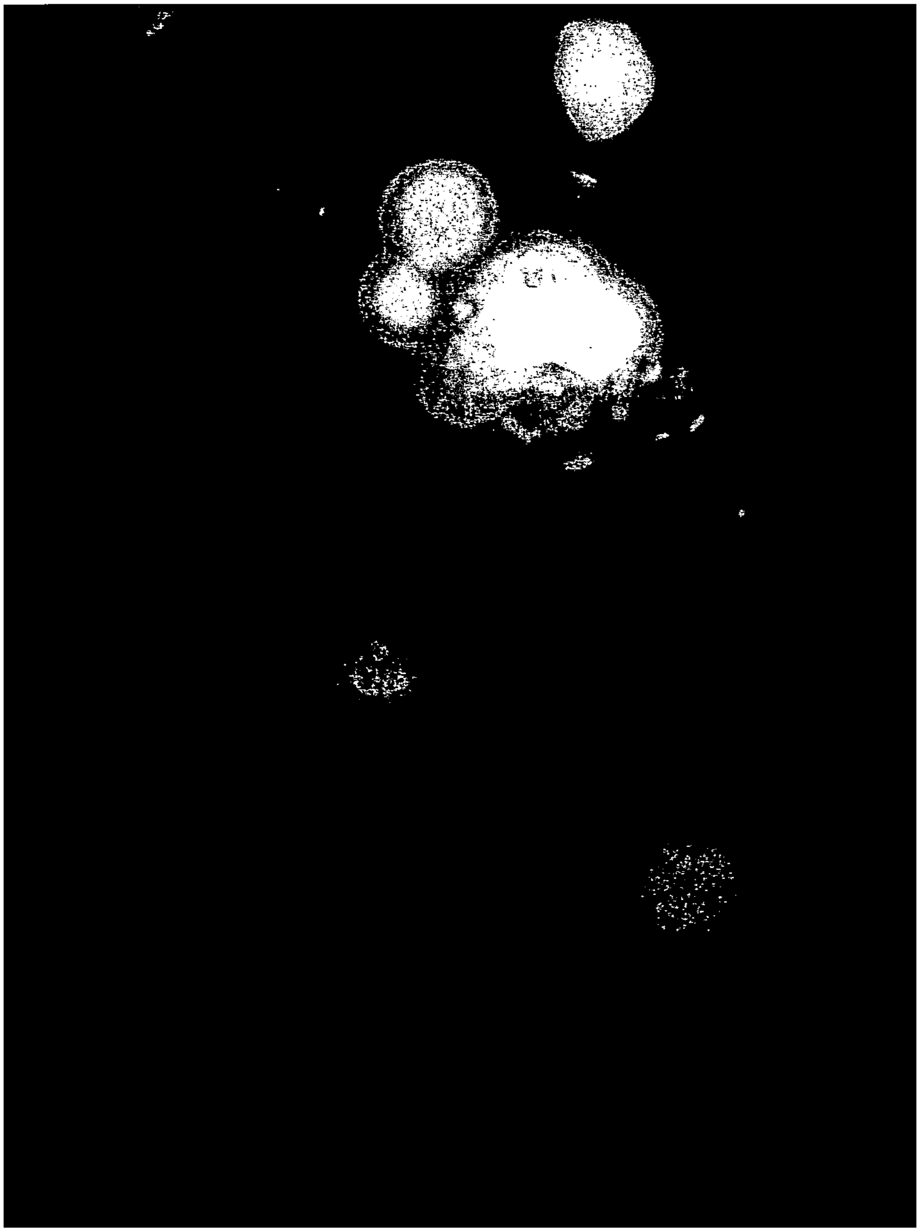
Figure 7B. H1 derived occlusion of GFP

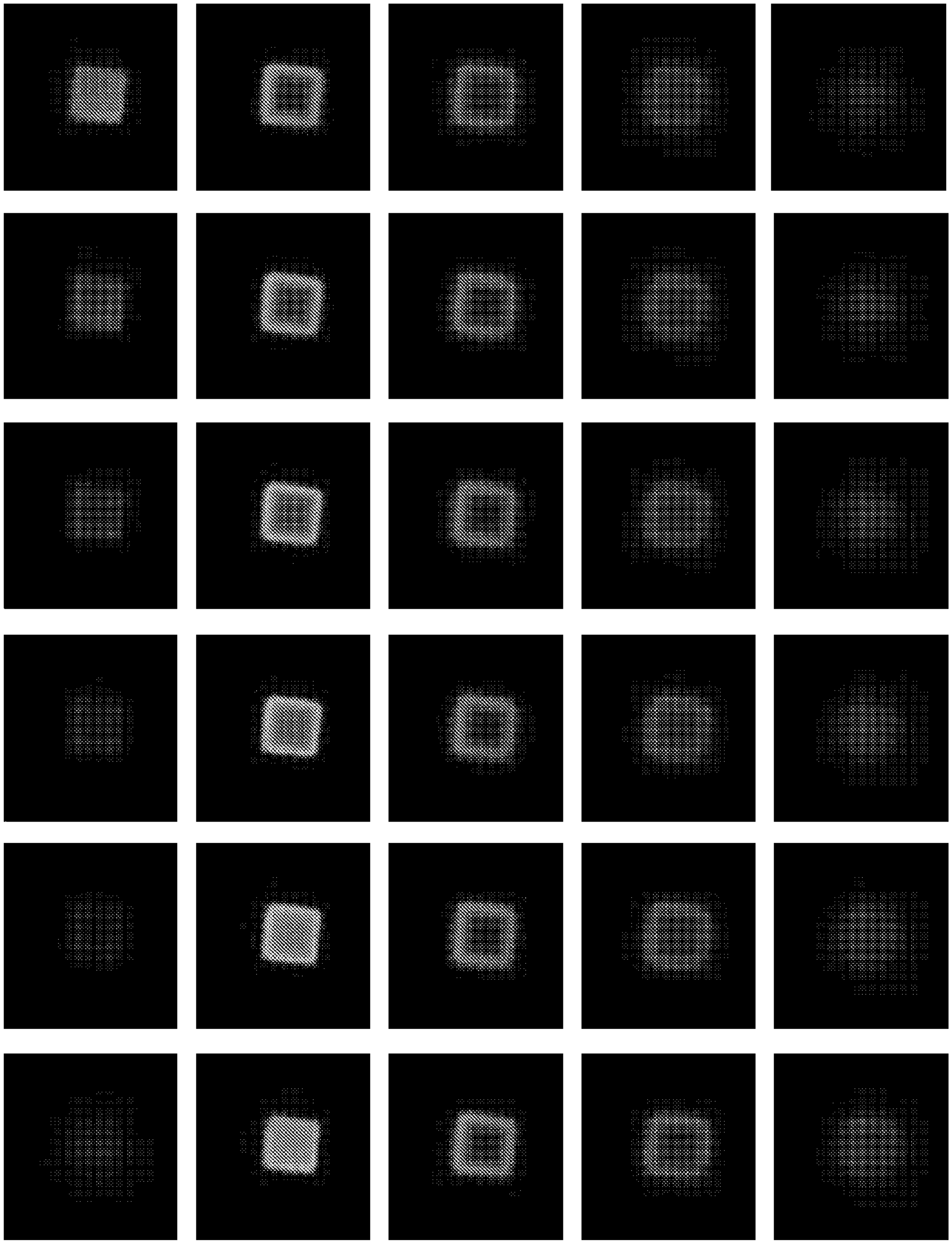
Figure 8. Co-expression of H1-EGFP and CPV polyhedrin

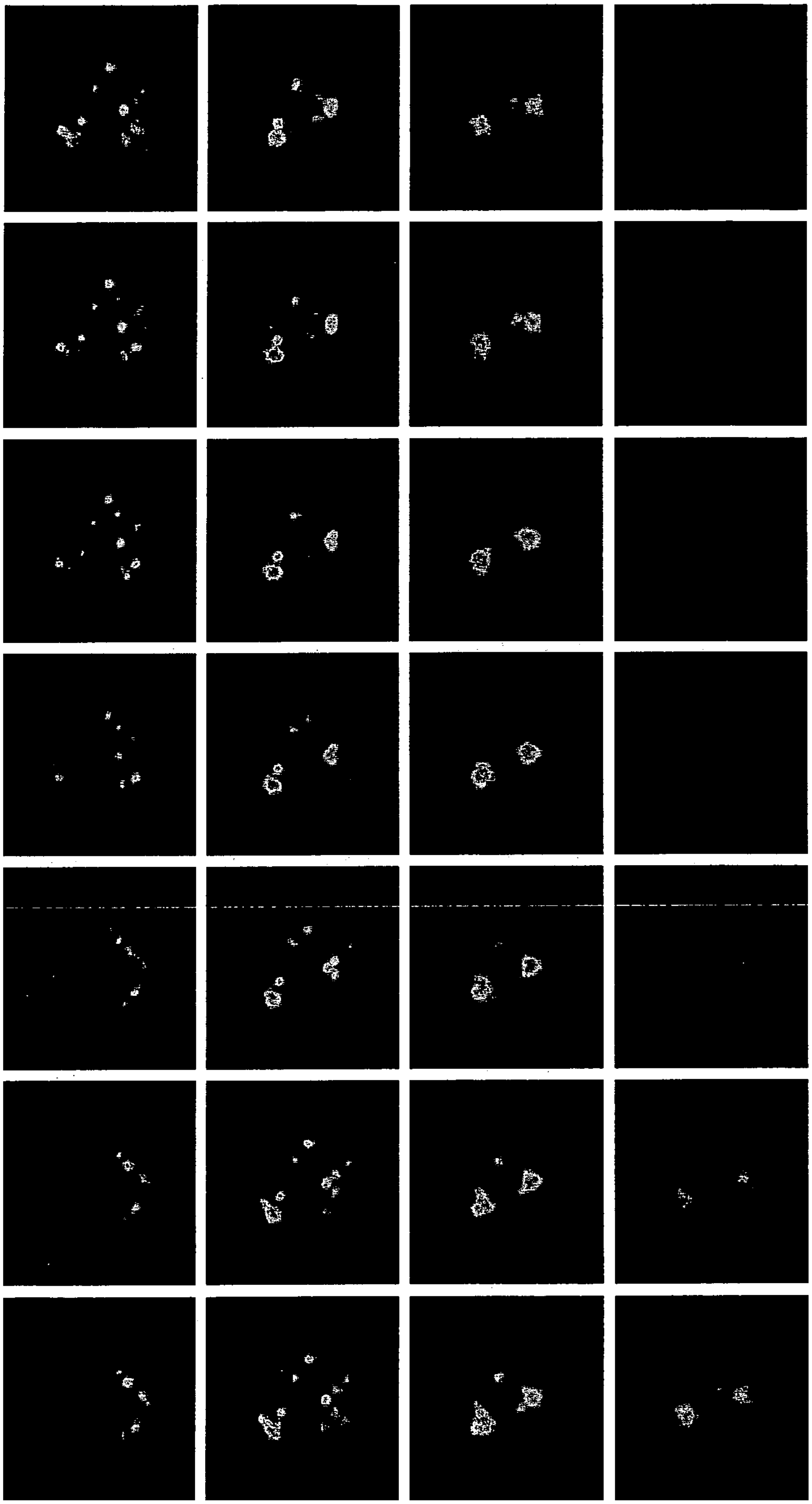
Figure 9. Addition of H1GFP to CPV polyhedra

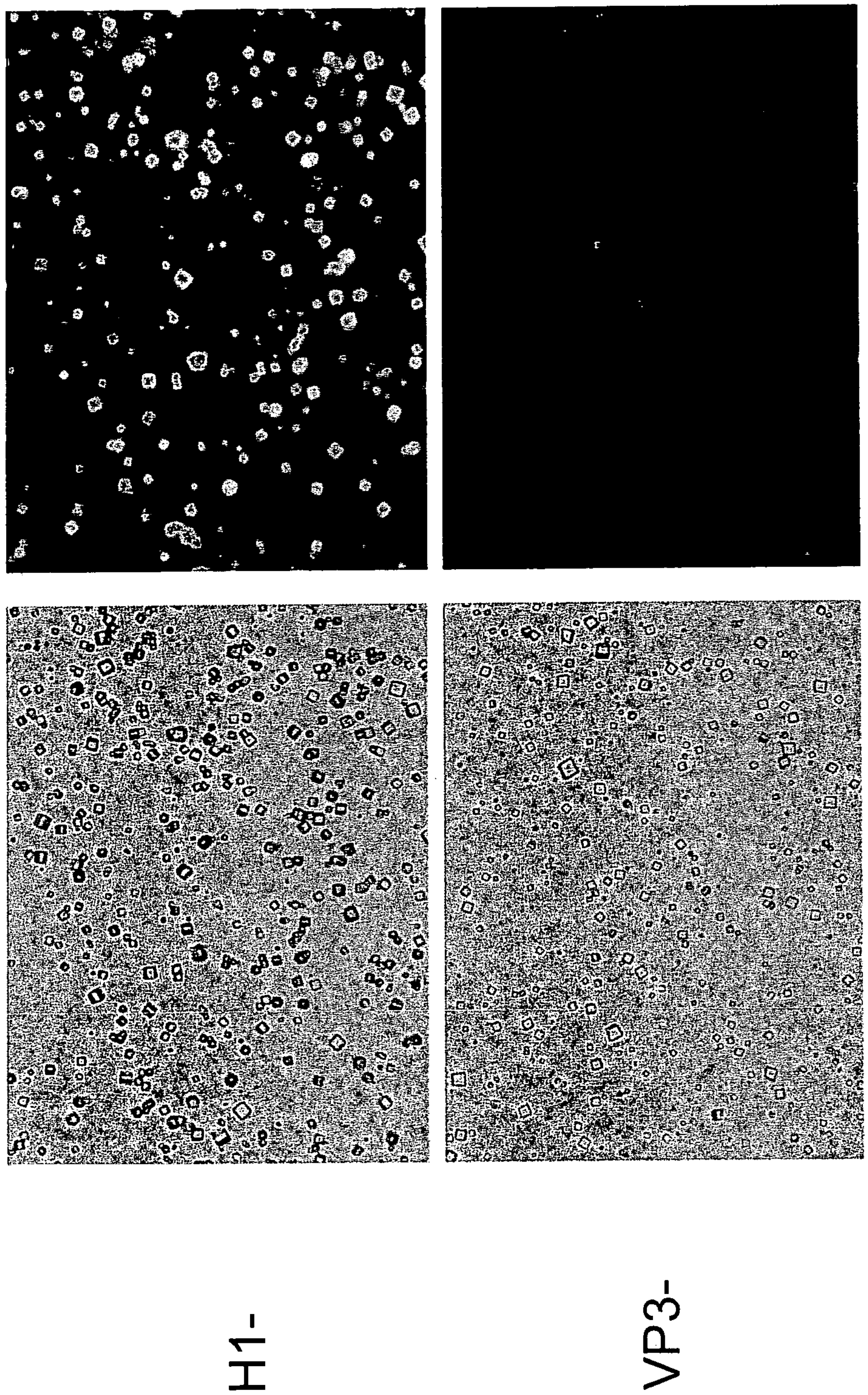
Figure 10. The green fluorescence from the polyhedra in which H1-GFP and VP3-GFP was immobilized.

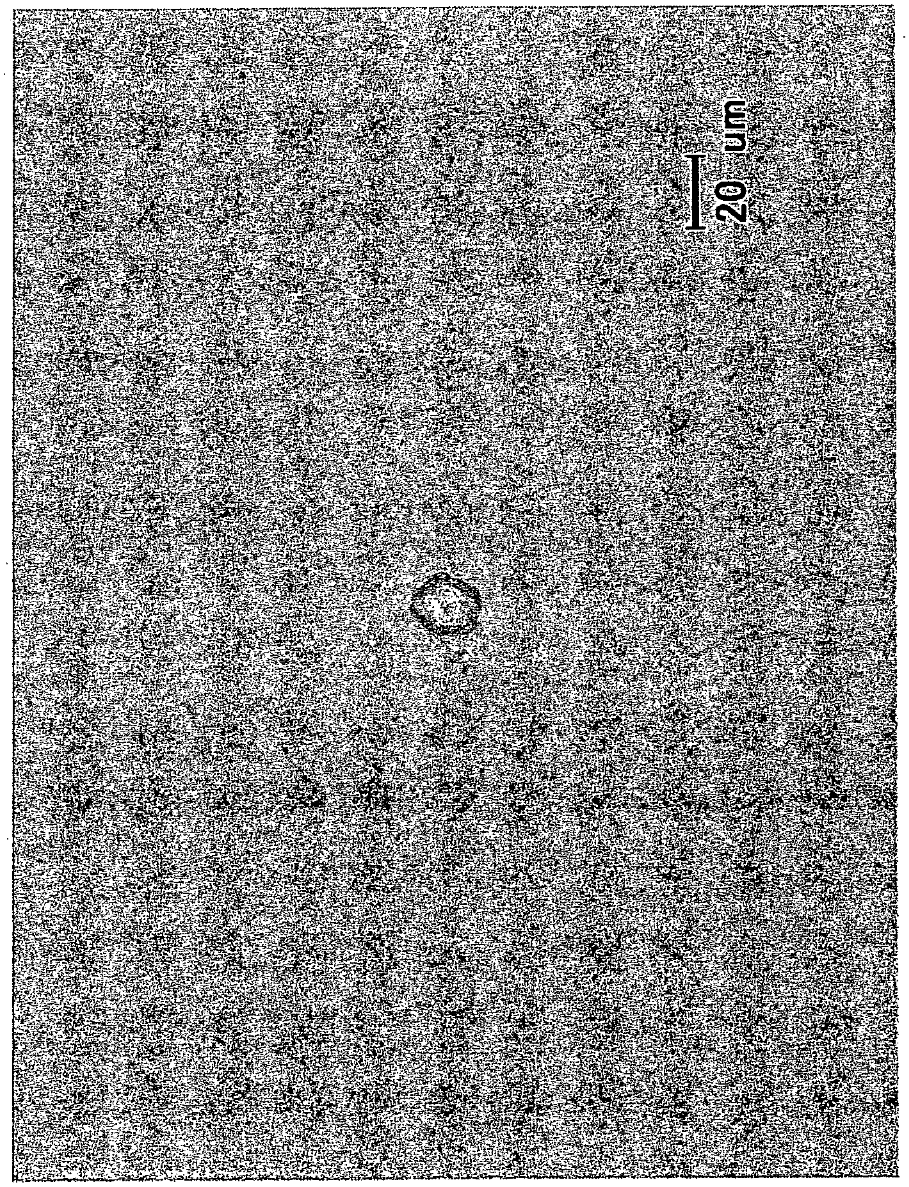
Figure 11. Crystallization of H1-GFP.
1.5M Ammonium Sulfate, 15% Glycerol, 0.1M Tris-HCl pH8.5
2 days after hanging drop Fig. 12 Cell proliferation assay by H1-FGF2 polyhedra
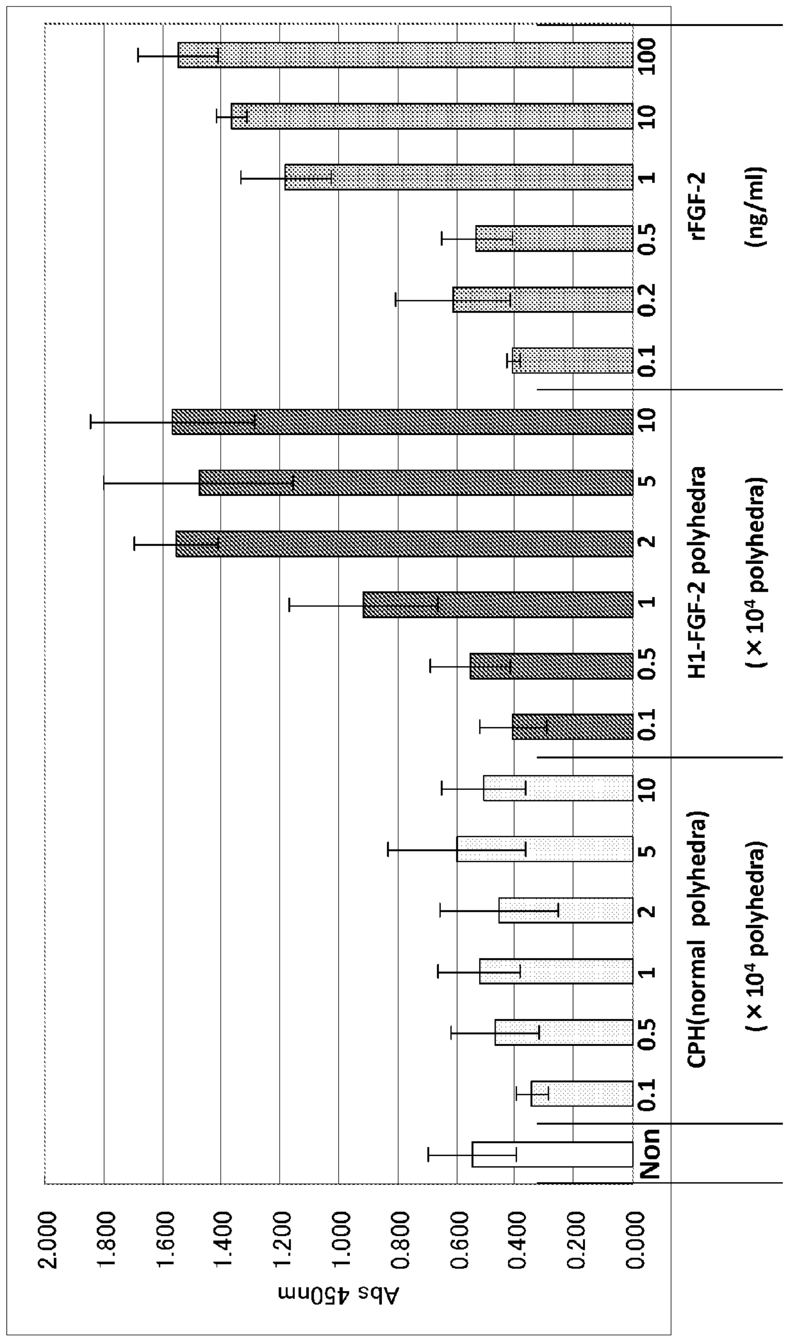
NIH3T3 cells were seeded onto 96-well plate at a density of 4000cells/well and cultured overnight in DME medium containing 10% FBS. Cells were then starved α-ME medium without FBS and cultured in the presence of normal polyhedra, H1-FGF-2 polyhedra, or recombinant liquid FGF-2.

Cell proliferation assay by H1/FGF-7 polyhedra

Polyhedra were dried up onto 96-well plate at a each density normal polyhedra and H1/FGF-7 polyhedra.

NHEK (Normal human epidermal keratinocyte) cells were seeded onto 96-well plate coated with dried polyhedra at a density of 2500cells/$cm^2$ and cultured in Defined K-Serum Free medium (DK-SFM) without supplement.

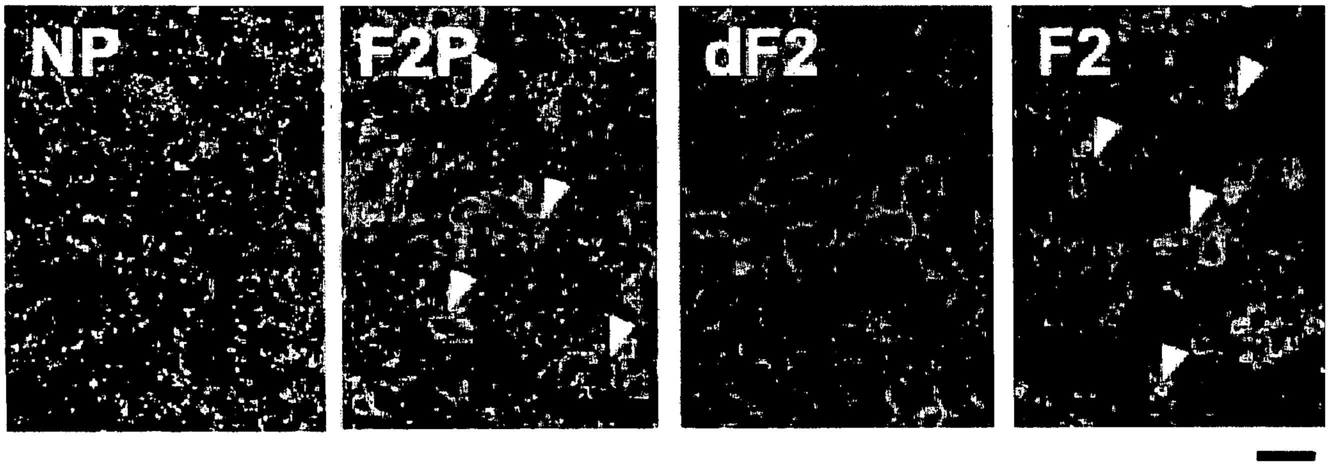
Figure 14 Include Title
Thermanox coverslips were spotted with desiccated NP, F2P, or F2 and placed in 8-well plates, into which ATDC5 cells were seeded at a density of 1x104 cells per well. After 2 days incubation, the effects of these treatments on the proliferation of the cells were investigated.
Scale bar, 100 μm.

VIRAL POLYHEDRA COMPLEXES AND METHODS OF USE

TECHNICAL FIELD

The present invention relates to a method of introducing target molecules into a polyhedron or part thereof. The invention also relates to complexes formed by introducing target molecules into polyhedron or part thereof and to polyhedrin protein variants that are useful in the methods of the invention. The invention also relates to the use of the methods, complexes and polyhedrin protein variants for the stabilization of proteins in particular, for cell culture, biosensors, microarrays, and assays.

BACKGROUND

Any discussion of the prior art throughout the specification should not be considered an admission that such prior art is widely known or forms part of common general knowledge in the field.

Stable maintenance of molecules, and in particular functional molecules, on support surfaces can be critical for analytical and diagnostic tools—for example, in high throughput analysis and functional characterization of biomolecules. However, techniques for stably immobilizing and preserving functional proteins, biomolecules and biosensors on support surfaces have not been optimised.

For DNA chips, designing capture molecules and developing read-out systems is relatively straightforward. DNA or oligonucleotides bind specifically to complementary mRNA sequence tagged with a fluorescent dye. However, designing arrays for proteins is more complex and requires different consideration. Proteins must be immobilized on the surface of the chip such that they retain their native conformation and also such that their active site(s) are exposed rather than buried. Constructing a protein chip therefore involves more steps and more complex protein chemistry. The following are some of the issues to consider when building a useful protein chip: 1) immobilization of proteins of diverse types such that they retain their secondary and tertiary structure, and thus their biological activity; 2) identification and isolation of an agent with which to capture the proteins of interest; 3) a means of measuring the degree of protein binding, ensuring both sensitivity and a suitable range of operation; and 4) extraction of the detected protein from the chip and analysis of the protein.

Many prophylactic and therapeutic agents require special conditions to protect them from environmental damage during transportation and storage. This adds to the cost of the drug and, in certain instances, reduced availability in some communities eg. in remote and/or disadvantaged communities where conditions such as low temperature cannot easily be achieved during transportation over long distances.

Further, there is a continuing need for new pharmaceutical formulations, excipients, and delivery devices, including nanodevices, to achieve maximum benefit from drugs. For example, slow release and/or organ-/tissue-specific release of prophylactic and therapeutic agents can provide increased drug efficacy, improve bioavailability and reduce drug dosage. There is a need for versatile and safe means for administering agents intact and with site-specific and dose-specific accuracy.

Cytoplasmic Polyhedrosis Viruses

Insect virus infections result in the production of massive amounts of large protein crystals (occlusion bodies), termed polyhedra and many virus particles are occluded within the polyhedra. An insect virus, cypovirus (cytoplasmic polyhedrosis viruses, CPV), is classified among the family Reoviridae and has a segmented genome composed of ten double-stranded RNAs. The virion consists of an icosahedral protein shell of 50-70 nm in diameter and twelve spikes on the 12 vertices of the shell. Polyhedra are the main vectors of virus particle transmission from insect to insect and are the main agents of survival of the virus between one insect generation and the next because they stabilize virions, allowing them to remain viable for long periods in the environment. Infection occurs when an insect ingests the alkali-soluble occlusion body and the virus particles are released by the high pH of the insect intestine.

The virus particles of CPVs and baculoviruses produce micro-sized protein crystals called polyhedra in which virus particles can be embedded (Belloncik and Mori 1998; Miller 1997). Polyhedra exhibit remarkable stability and, as such, the embedded insect viruses can remain infectious for years in the environment. The virus particles are embedded in the polyhedron via the constituent CPV envelope protein, VP3, which binds to the polyhedrin protein, the major viral protein making up the polyhedron.

The improved stability of viral particles within the polyhedra has prompted studies investigating whether target proteins can be embedded within polyhedra for improving their stability and facilitating their use in protein microarray applications (US20060155114 and Ikeda et al 2006). This approach involved co-expressing target proteins fused to a portion of a virion structural capsid protein, VP3 during CPV infection. The results indicated that incorporation of these proteins into the polyhedron crystal was successful and that the proteins were protected from dehydration and stabilized against high temperatures without the loss of function. Proteins that have been incorporated into polyhedra using the VP3, are non-membrane and membrane proteins including, enzymes such as polymerases, kinases and acryltransferases; structural proteins such as ribosome proteins and ribosome binding proteins; and transcription factors; and elongation factors. Accordingly, the skilled addressee would understand that a diverse range of different types of molecules may be incorporated into a polyhedron without the loss of function.

Although these unique protein crystals have been characterised since the early 1900s (Glaser and Chapman 1916) determination of their atomic structure which would allow for the further development of the polyhedra into useful diagnostic, therapeutic and research tools has been elusive. Further there has been no suggestion that exogenous molecules such as proteins can be incorporated into a polyhedron crystal in the absence of a virion structural protein tag. There has been no suggestion that molecules may be incorporated into a polyhedron in locations other than that usually occupied by virus particles.

It is an object of the present invention to overcome or ameliorate at least one of the disadvantages of the prior art, or to provide a useful alternative.

SUMMARY OF THE INVENTION

Protein structure determination of polyhedra has been hampered by the small size of the crystals and a number of other factors. Surprisingly, the 2 Å crystal structures of both recombinant and infectious silkworm CPV polyhedra have now been determined using 5-12 micron crystals purified from insect cells. These are the smallest crystals yet used for de novo X-ray protein structure determination (Riekel et al 2005).

A number of features of the structure became apparent that had previously not been recognised. It was unexpectedly found that some of these features could facilitate the accommodation of target molecules within a polyhedron crystal.

It was found that polyhedra are made of trimers of the viral polyhedrin protein and contain nucleotides. Although the shape of these building blocks is reminiscent of some capsid trimers, polyhedrin has a new fold and has evolved to assemble in vivo into 3-D cubic crystals rather than icosahedral shells. The polyhedrin trimers are extensively cross-linked in polyhedra by non-covalent interactions and pack with an exquisite molecular complementarity similar to that of antigen-antibody complexes. The resulting ultra-stable and sealed crystals shield the virus particles from environmental damage. The structure suggests that polyhedra can serve as the basis for a large number of applications including the development of robust and versatile nanoparticles for biotechnological applications (Douglas and Young 2006) such as microarrays (Ikeda et al 2006) and bio-pesticides (Chang et al 2003).

Specifically, it has been found that the crystal structure of the cypovirus polyhedra facilitates the identification of regions of the polyhedrin protein that play central roles in the architecture of the crystal structure and that attaching at least a portion of these regions to a target molecule allows the target molecule to be sequestered by the polyhedron crystal—either by incorporation into the lattice structure or by attachment to the surface of the crystal.

As such, the present invention relates to novel complexes, methods for their production and uses thereof that may, in certain embodiments, preserve, prolong or protect the functionality of a target molecule by complexing the target molecule within a polyhedron or part thereof.

In one embodiment, a fusion protein comprising a target molecule and at least a portion of a polyhedrin protein may be co-expressed with the necessary proteins to produce a polyhedron complex comprising the fusion protein.

In an alternative embodiment, a fusion protein comprising a target molecule and at least a portion of a polyhedrin protein may be added to a polyhedron and as a result the fusion protein is incorporated into the polyhedron.

The use of the crystal structure of the CPV polyhedra in the present invention confers advantages not previously recognised or contemplated.

Accordingly, in a first aspect, the present invention provides use of co-ordinates of a cytoplasmic polyhedrosis virus (CPV) polyhedron crystal structure in the design and/or manufacture of (a) a modified polyhedron or part thereof, or (b) a complex comprising the polyhedron or part thereof.

In a second aspect, the present invention provides a method of preserving, prolonging or protecting the functionality of a target molecule the method comprising the following steps:

(i) using the coordinates of a CPV polyhedron crystal structure to identify a region of interest in the polyhedron; and (ii) preparing a fusion molecule comprising the target molecule and at least a portion of the region of interest such that the fusion molecule is adapted for inclusion in a polyhedron crystal or part thereof.

In one embodiment the region of interest is contributes to the architecture of the polyhedron crystal structure. Preferably, the region of interest comprises an N-terminus H1 helix of a polyhedrin protein or functional equivalent thereof. In a particularly preferred embodiment the region of interest comprises SEQ ID No 6 or functional equivalent thereof.

In a third aspect the present invention provides a method of preparing a modified polyhedron or part thereof the method comprising the steps of:

(a) using the co-ordinates of a CPV polyhedron crystal structure to identify a region of interest;

(b) preparing a fusion molecule comprising a target molecule and the region of interest or portion thereof such that the fusion molecule is adapted for inclusion in a polyhedron crystal or part thereof;

(c) incorporating the fusion molecule into a polyhedron.

In one embodiment the fusion molecule is incorporated into a polyhedron by contacting the fusion molecule with a polyhedron. In an alternate embodiment the fusion molecule is incorporated into a polyhedron by co-expressing the fusion molecule with a polyhedron.

In a fourth aspect the present invention provides: a modified polyhedron produced by the method according to the invention.

In a fifth aspect the present invention provides a complex comprising a polyhedron or part thereof and a fusion molecule the fusion molecule comprising a target molecule and a polyhedrin protein or portion thereof.

In one embodiment the complex does not include an encapsulated virus particle.

Preferably, the polyhedrin protein is an N-terminal H1 helix of the polyhedrin protein or a functional equivalent thereof. Most preferably, the polyhedrin protein comprises SEQ ID No 6 or a functional equivalent thereof.

In an alternative embodiment, the complex comprises a polyhedron or part thereof and two fusion molecules wherein one fusion molecule includes at least a portion of a VP3 capsid protein of CPV and the other fusion molecule includes at least a portion of the N-terminal H1 helix of the polyhedrin protein.

In a sixth aspect the present invention provides a use of a modified polyhedron or part thereof according to the invention or a complex according to the invention wherein the modified polyhedron or part thereof or the complex or part thereof is applied to a solid surface to produce an active surface and the functionality of the target molecule on the active surface is prolonged, protected or retained.

In one embodiment the modified polyhedron or part thereof or the complex or part thereof is desiccated on the active surface. Preferably, the active surface is used in a medium or is in contact with a medium for culturing cells. More preferably, the target molecule or functional equivalent thereof is released from the active surface into the medium such that replenishment of the medium with the target molecule is not required.

In an alternative embodiment, the active surface is used in an assay. Preferably the assay is a microarray assay.

Preferably the target molecule incorporated in modified polyhedron or part thereof or the complex or part thereof is selected from the group consisting of a polypeptide, a protein, a glycoprotein, a carbohydrate, a nucleotide, a nucleic acid, a lipid, a lipoprotein, a drug, a cytokine, an antigen, an antibody, an antibody fragment, a fluorescent molecule, a dye, a pH sensitive molecule a toxin, a venom and a bioactive molecule. More preferably, the target molecule is a growth factor and most preferably a fibroblast growth factor. In a particularly preferred embodiment the target molecule is selected from fibroblast growth factor-2 or fibroblast growth factor-7.

In a seventh aspect the present invention provides a cell culture system or component of a cell culture system comprising a modified polyhedron or part thereof according to the invention or a complex or part thereof according to the invention. In certain embodiments the cell culture system can comprise any vessel adapted for culturing cells such as a cell culture plate, a roller bottle, a fermentation culture system or a bioreactor.

In an eighth aspect the present invention provides a method of culturing cells comprising contacting the cells with a medium that comprises or is in contact with a modified polyhedron or part thereof according to the invention or a complex or part thereof according to the invention.

In a ninth aspect the present invention provides an assay comprising a modified polyhedron or part thereof according to the invention or a complex or part thereof according to the invention. Preferably, the assay is a microarray assay.

In a tenth aspect the present invention provides a biosensor comprising modified polyhedron or part thereof according to the invention or a complex according to the invention. Preferably, the bio sensor is a pH sensor.

Immobilization of biomolecules is a key procedure in many biotechnological tools, including biochips and biosensors. See, e.g., Drummond et al. (2003); Zhu et al. (2003); Wulfkuhle et al. (2003); Tirumalai et al. (2003). Different approaches have been developed to anchor biomolecules on solid supports.

Bio-recognition biosensors may be classified into immunochemical, enzymatic, non-enzymatic receptor, and DNA biosensors. Immuno-sensors are very sensitive, selective and versatile since antibodies can be generated to bind a wide range of compounds that are structurally different. In general, enzymatic biosensors are based on the selective inhibition of specific enzymes by different classes of compounds, with the decrease in activity of the immobilized enzyme in the presence of the target molecule as the parameter that is frequently used for quantification. There is a wide range of enzymes suitable for acting as recognition elements and very often their catalytic properties or substrate specificity can be modified by means of genetic engineering. Biosensors based on natural receptors can be built by integrating the specific receptor within a membrane and by coupling it to a transducing device. These natural receptors are proteins of non-catalytic or non-immunogenic origin, which span cell membranes and can specifically bind certain compounds. One of the limitations of these biosensors is that the biosensor reaction takes place on a solid support platform and there is a need to enhance the stability or preserve the functionality of bioactive molecules on these solid supports.

The advantage of the polyhedra biosensor and bioassay of the present invention lies in the stabilisation and/or the maintenance of active target molecules on a support platform. This would involve the complex comprising the polyhedra-embedded target molecule being bound to a support surface and binding to, or interacting with, molecules in a biological or environmental sample then detecting the binding or interaction.

The identification, analysis and monitoring of biological molecules (such as polypeptides, polynucleotides, polysaccharides and the like) or environmental molecules (such as pesticides, bio-warfare agents, food contaminants and the like) has become increasingly important for research and industrial applications. Conventionally, molecule detection systems are based on molecule-specific binding between a molecule and an molecule-binding receptor. Such systems typically require complex multi-component detection systems (such as ELISA sandwich assays) or electrochemical detection systems, or require that both the molecule and the receptor are labelled with detection molecules One method for detecting molecule-binding agent interactions involves a solid phase format employing a reporter labelled molecule-binding agent whose binding to, or release from, a solid surface is dependent on, the presence of molecule. In a typical solid-phase sandwich type assay, for example, the molecule to be measured is a molecule with two or more binding sites, allowing molecule binding both to a receptor carried on a solid surface (the target molecule in the polyhedra), and to a reporter-labelled second receptor. The presence of the molecule is detected based on the presence of the reporter bound to the solid surface.

In an eleventh aspect the present invention provides a bio-pesticide comprising a modified polyhedron or part thereof according to the invention or a complex according to the invention. For the bio-pesticide embodiment the target molecule is detrimental to a host insect. In a particularly preferred embodiment the target molecule is a toxin from *Bacillus thuringiensis.*

Three strategies have been used to improve the efficacy of insect viruses as pesticides.

(a) Inactivation or deletion of genes from the viral genome that prolong the life of the host (e.g., U.S. Pat. No. 5,858,353).
(b) Use of the virus to stimulate inappropriate expression of host genes to deregulate physiological or developmental processes reviewed in Black et al., "Commercialization of Baculoviral Insecticides" in Miller, L. (ed.), The Baculoviruses, 1997)
(c) Engineering insect viruses to express insecticidal toxins, eg venom of natural host predators.

Potential disadvantages of the above include that they require establishment of a productive infection involving viral replication in order to be effective.

In contrast, a polyhedra complex according to the present invention comprising insecticide toxin may be sufficient to kill the host insect without the initiation of viral replication.

In the context of the present invention, the term "target molecule" includes, but is not limited to, a polypeptide, a protein, a glycoprotein, a carbohydrate, a nucleotide, a nucleic acid, a lipid, a lipoprotein, a drug, a cytokine, an antibody, an antibody fragment, a fluorescent molecule a dye, a pH sensitive molecule or a bioactive molecule, a growth factor a chemokine or a mitogen.

In the context of the present invention, the term "complex" includes, but is not limited to, the linkage of two or more agents by covalent or non-covalent binding, by ionic or non-ionic binding or by van der Waals forces.

In the context of the present invention, the words "comprise", "comprising" and the like are to be construed in their inclusive, as opposed to their exclusive, sense, that is in the sense of "including, but not limited to".

a, Scanning electron micrographs of recombinant (left) and infectious (right) polyhedra. Both crystals are made up of densely packed 103 Å unit cells (FIGS. 2 and 3) but the indentations on the surface of infectious polyhedra are due to virus particles which replace blocks of at least 300 unit cells. b, Polyhedrin has the shape of a left hand (inset). The finger (H1, blue), thumb (H4, orange), fist (S1-S2, cyan and S3, red) and clamp (H3, green) all contribute to the organization of polyhedra. c and d, The polyhedrin trimer in two orthogonal views with bound nucleotides shown in a yellow surface. The insets represent trimers with one of the subunits highlighted.

Figure 2:
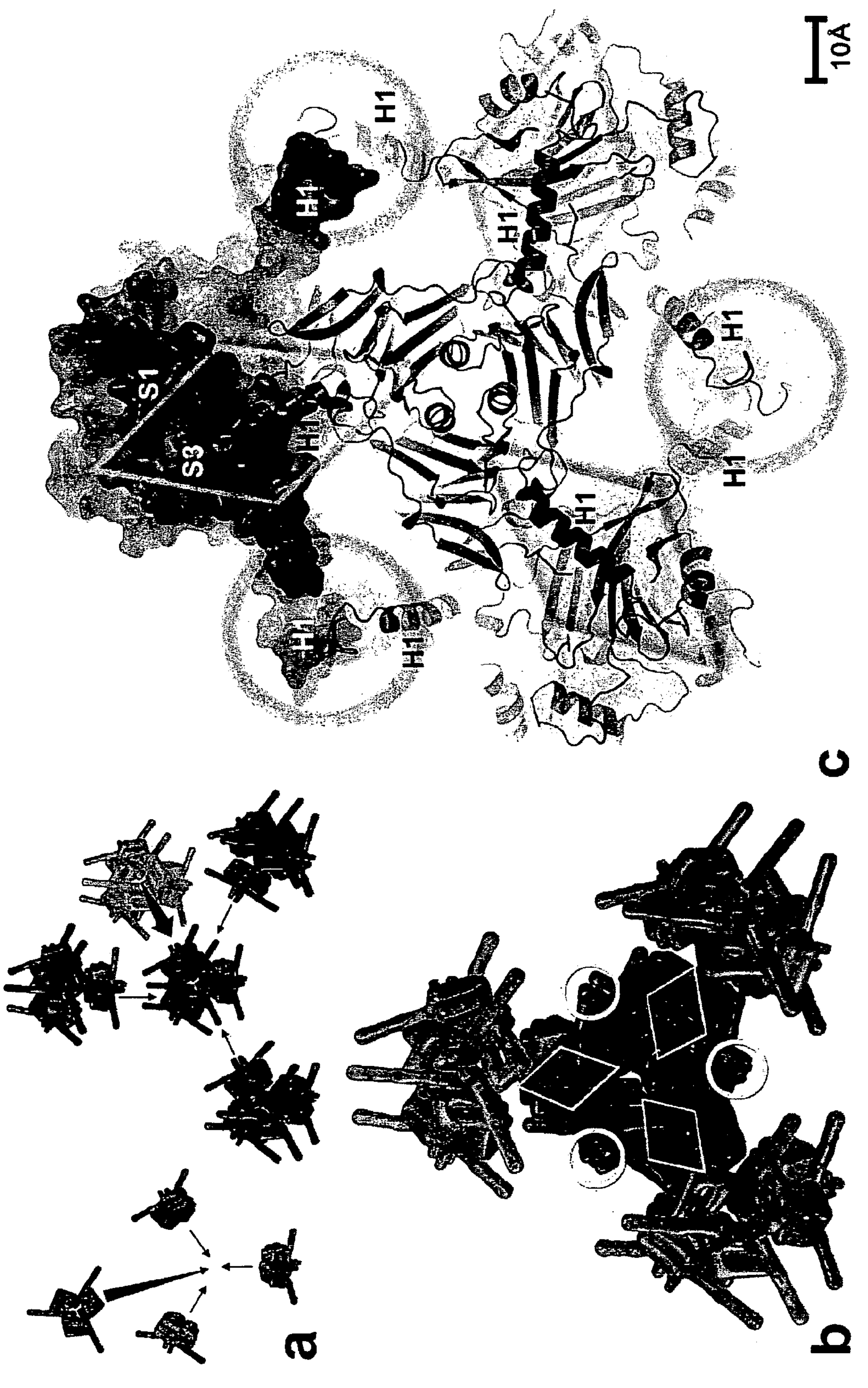

FIG. 2 Polyhedra are built around a tight scaffold of H1 helices.

a, Four polyhedrin trimers assemble around each lattice point of polyhedra to form a central tetrahedral cluster (blue hands). These clusters then pack tightly to form the body centered cubic crystal. b, c Schematic and molecular models of the crystal packing along the 3-fold axis of a trimer. The eight trimers of one I23 unit cell are highlighted in b. Two of the non-covalent interactions cross-linking trimers in polyhedra are shown as diamonds (finger-fist interactions) and circles (finger-finger interactions).

Figure 3:
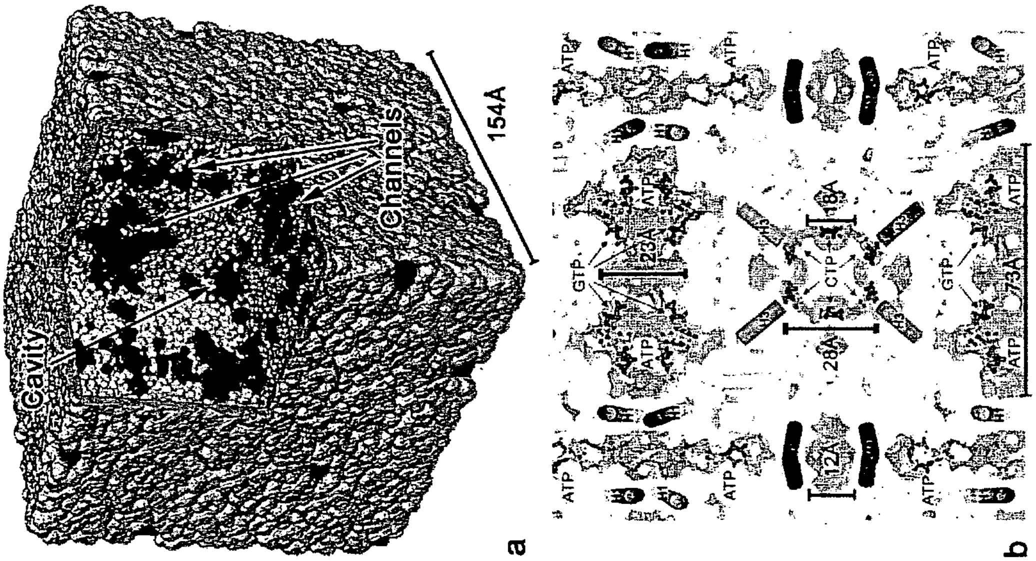

FIG. 3 Polyhedra are dense and sealed microcrystals containing nucleotides.

a, The continuous protein matrix of the unit cell is represented as a brown surface and grey spheres. The dense packing leaves only narrow solvent channels and a central cavity (red surface) blocked by H1 helices (blue cylinders). These blocks are repeated along the lattice, interrupted by the presence of virus particles. b, Mesh representation of the solvent channels and the central cavity. The ATP and GTP molecules located in the channels and the CTP molecules bound in the central cavity are represented as sticks. H1 and H3 helices are shown as blue and green cylinders respectively.

Figure 4:
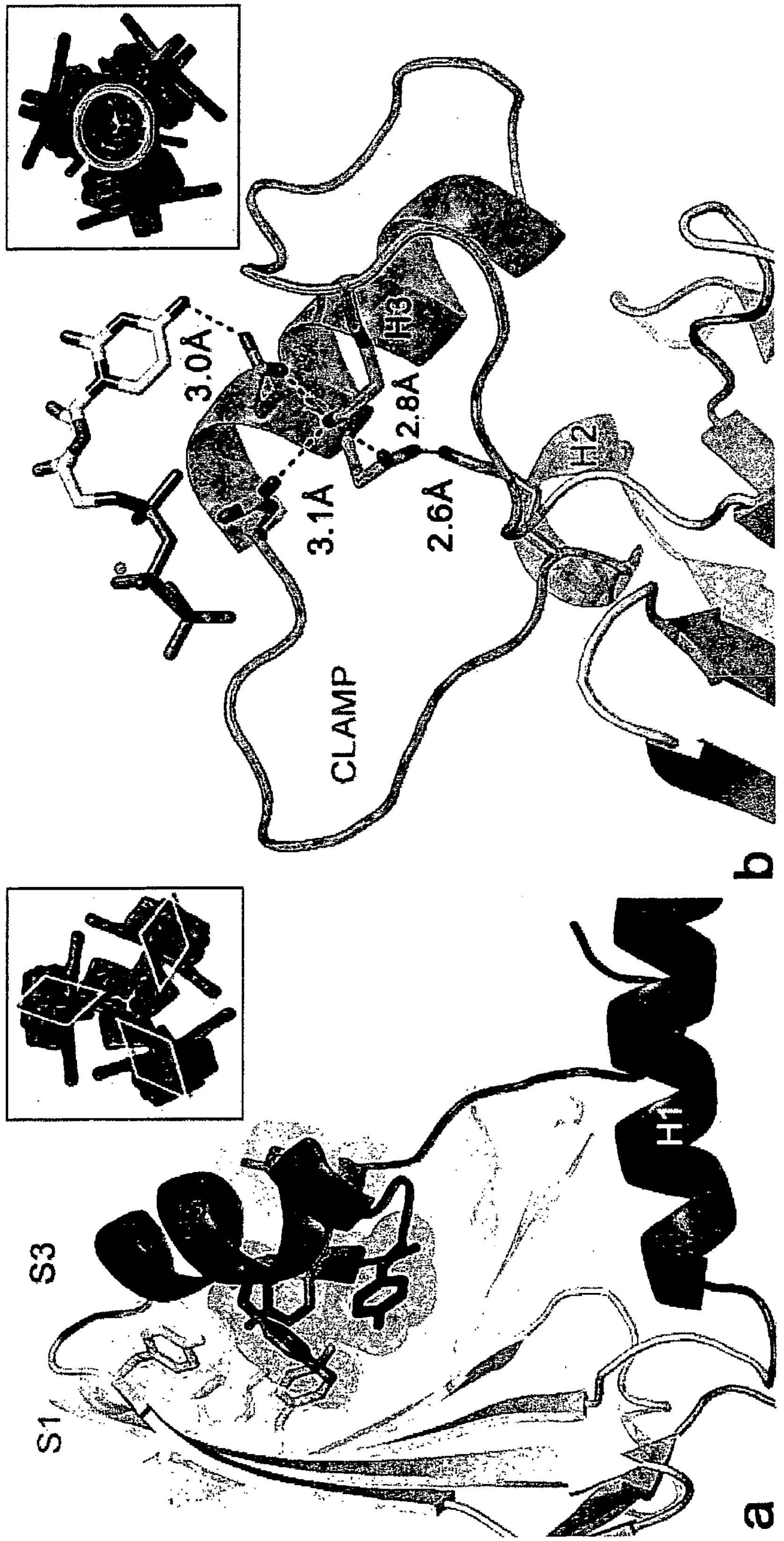

FIG. 4 Proposed mechanism for the release of virus particles

Unpaired buried negative charges are introduced at pH>10.5 in a tyrosine cluster found between S1 and S3 (a) and in a chain of salt bridges (residues K69-E82-K99-D81-D78) of the clamp (b). These regions, circled in the insets, are important in the packing of polyhedra and we propose that their disruption leads to dissolution of the crystal and release of the virus particles in the alkaline mid-gut of larvae.

Figure 5:
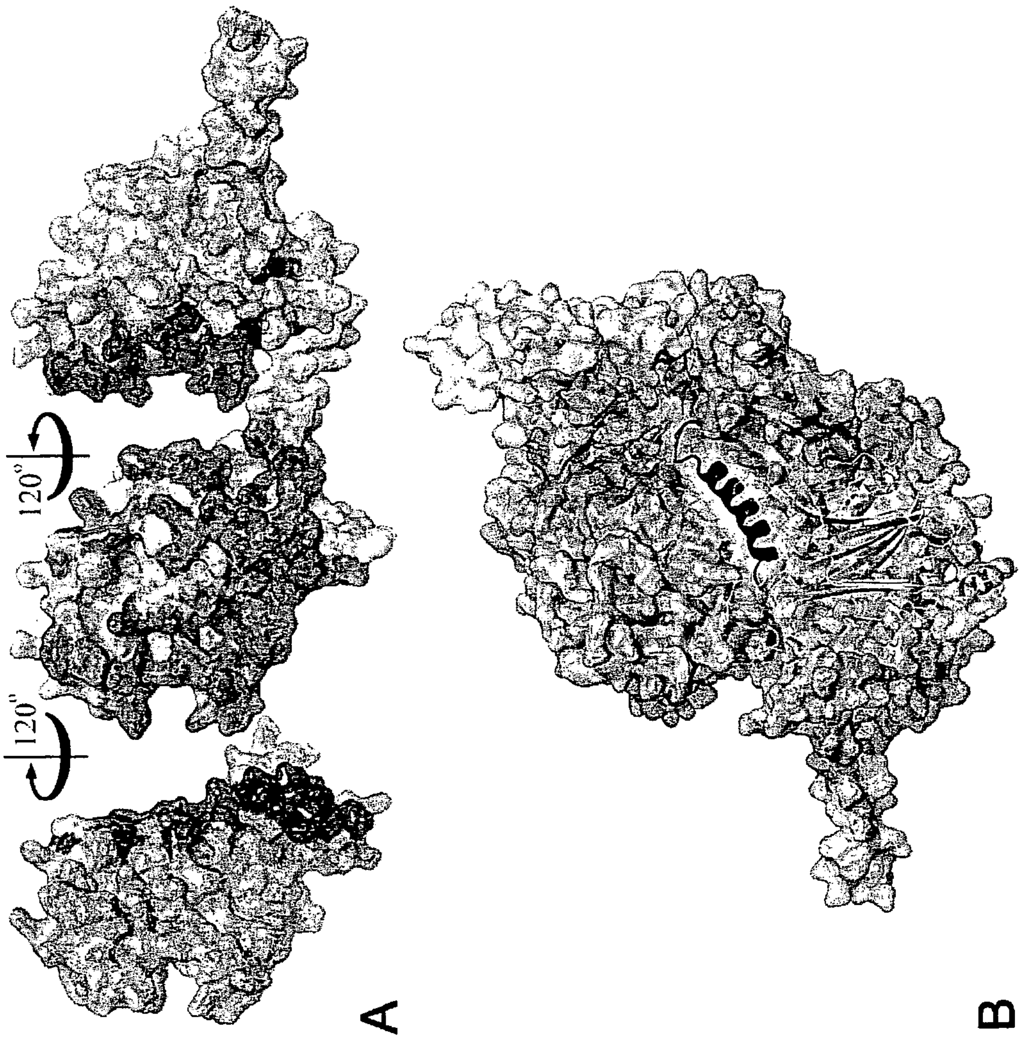

FIG. 5. Polyhedra are made from trimeric building blocks cross-linked by helix H1 a, Surface representation of the three subunits of a polyhedrin trimer. Two of the subunits have been rotated by +/−120° around the axes indicated by vertical bars to reveal the contact interfaces. These interfaces are coloured in red in the rotated subunits and coloured in blue and orange in the central polyhedrin molecule for residues involved in polar and hydrophobic interactions respectively. b, Helix H1 of a polyhedrin molecule highlighted in blue. Five different trimers are cross-linked by H1.

Figure 6:
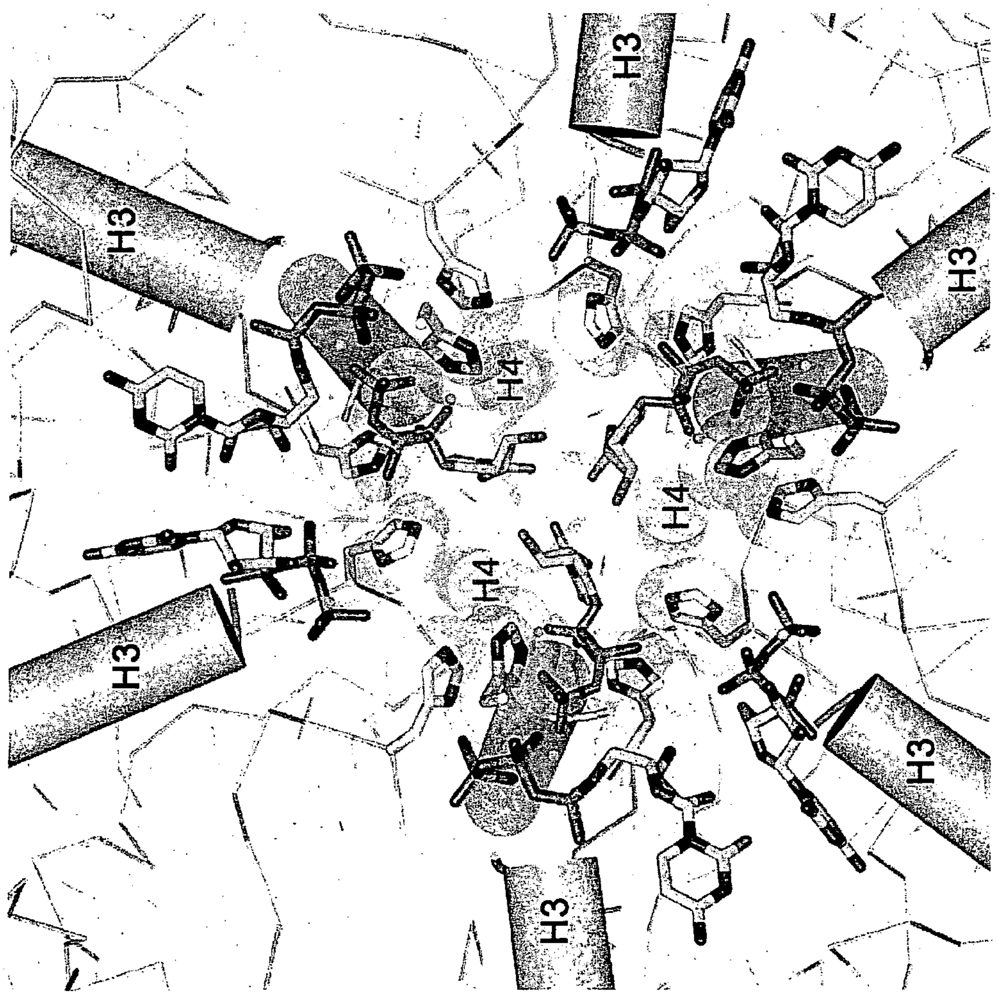

FIG. 6. The central cavity.

The central cavity viewed along a crystallographic 3-fold axis. The side chains of His76 and Phe201 are represented as sticks in molecular spheres. Helices H4 blocking the connection between neighbouring cavities are shown as orange cylinders. CTP molecules, shown as sticks, trapped in the cavity are bound at the N-terminal end of helices H3 (green cylinder). For clarity, the six front CTP were omitted and carbon atoms are yellow for the protein and cyan for CTP molecules.

FIG. 7 H1 derived occlusion of GFP

FIG. 8 Encapsulation of a H1/EGFP in the polyhedra by co-expression of the H1/EGFP with polyhedrin protein.

FIG. 9 Encapsulation of an H1/EGFP fusion molecule in polyhedra by incubation with polyhedra.

FIG. 10 The green fluorescence from the polyhedra in which H1/GFP and VP3/GFP was immobilized.

FIG. 11 Crystallization of H1-GFP.1.5M Ammonium Sulfate, 15% Glycerol, 0.1M Tris-HCl pH8.5

FIG. 12 H1/FGF-2 polyhedra stimulate the growth of epithelial cells.

Bar graphs showing growth stimulation of starved NIH3T3 cells in the absence of fetal calf serum when incubated with H1/FGF-2 polyhedra (centre graph), but not when incubated with control polyhedra (left graph, negative control experiment). H1/FGF-2 polyhedra function as a stable replacement for recombinant FGF-2 with equivalent activity in this assay (right graph, positive control experiment).

Figure 13:
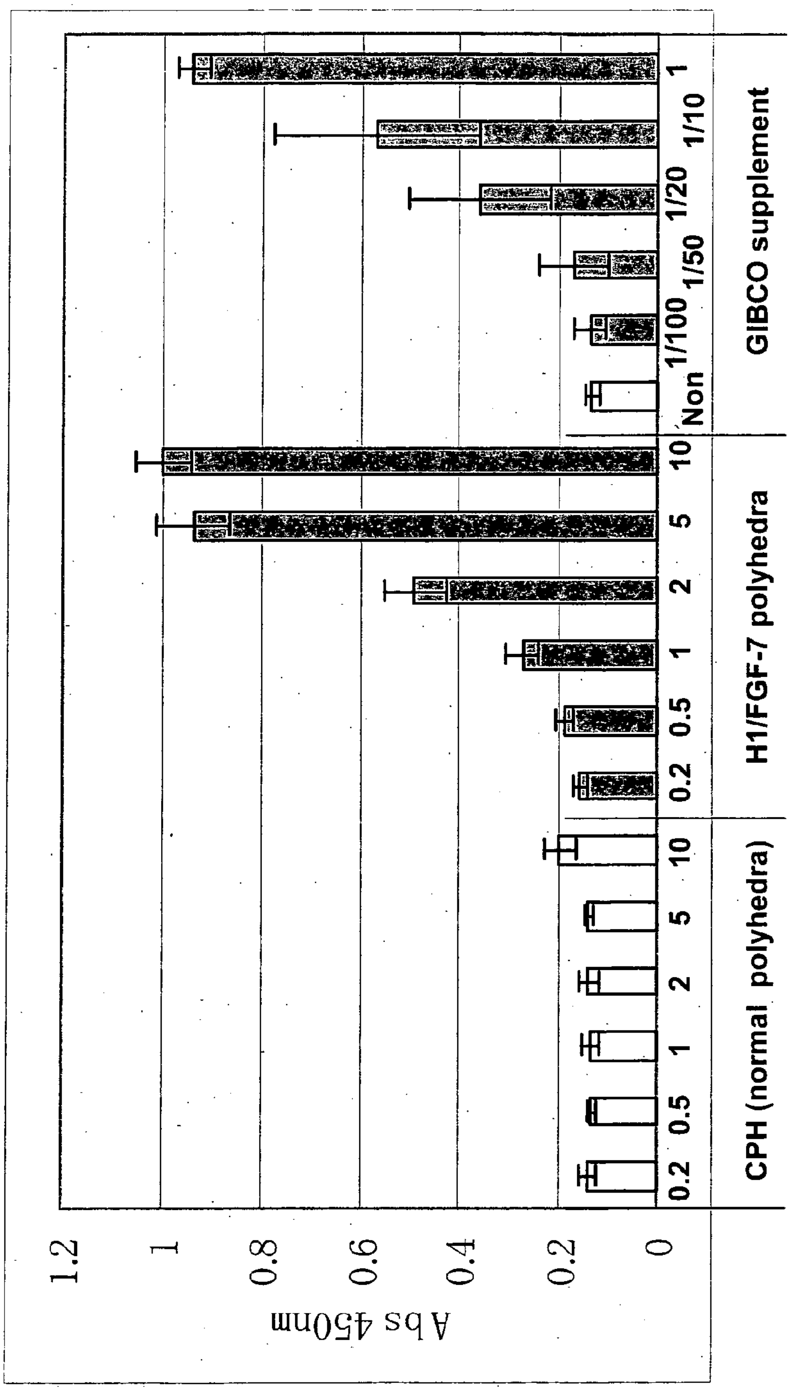

FIG. 13 H1/FGF-7 polyhedra stimulate the growth of keratinocytes.

Bar graphs showing growth stimulation of human epidermal keratinocytes (NHEK cells) with H1/FGF-7 polyhedra (centre graph) to levels similar to that achieved using fetal calf serum supplement (right graph, positive control experiment). Incubation with control polyhedra does not stimulate growth (left graph, negative control experiment).

FIG. 14 Stability of H1/FGF-2 immobilized into the polyhedra after desiccation.

Thermanox coverslips were spotted with unmodified polyhedra, H1/FGF-2 polyhedra and rFGF-2. After complete desiccation, the coverslips were placed in 8-well plates, into which ATDC5 cells were seeded at a density of $1\times10^4$ cells per well. After 2 days incubation, the effects of these treatments on the proliferation of the cells were investigated. NP, normal polyhedral; F2P, spotted and desiccated H1/FGF-2 polyhedra; dF2, spotted and desiccated rFGF-2; F2, rFGF-2.

DESCRIPTION OF THE INVENTION

Preferred embodiments of the invention will now be described with reference to the accompanying figures.

CPV and baculoviruses are notoriously difficult to eradicate because the virus particles are embedded in micron-sized protein crystals called polyhedra (Belloncik and Mori 1998 and Miller 1997). The remarkable stability of polyhedra means that like bacterial spores these insect viruses remain infectious for years in soil. The environmental persistence of polyhedra is the cause of significant losses in silkworm cocoon harvests but has also been exploited against pests in biological alternatives to chemical insecticides (Summers 2006; Chang et al 2003). Although these unique in vivo protein crystals have been extensively characterized since the early 1900s (Glasser and Chapman 1916), their atomic organization remained elusive (Rohrmann 1986).

CPVs are members of the Reoviridae, a virus family with characteristic icosahedral subviral particles that function as small 'replication machines' transcribing viral mRNAs from internal, segmented double-stranded RNA templates in the cytoplasm of infected cells (Fields et al 2001). CPV are the only known members of the Reoviridae where the virus particles are protected by polyhedra, each of which contains several thousand CPV particles (Bellonicik and Mori; 1998; Miller 1997; Rohrmann 1986; Zhang et al 1999; Hill et al 1999).

In the extracellular environment, virus particles embedded in polyhedra survive dehydration, freezing and enzymatic degradation (Rohrmann 1986). In addition, we found that polyhedra tolerate chemical treatments that would denature most proteins, including incubation in concentrated urea, acid and detergents, and still maintain their ordered crystalline organization (Table 1). By contrast, polyhedra dissolve readily when exposed to pH higher than 10.5 (Lawrence, M. C. & Colman 1993). The molecular basis of the remarkable stability of these in vivo crystals and how they are primed for disassembly in the alkaline mid-gut of insect larvae is unknown.

We developed methods for analyzing polyhedra suspended in thin layers of cryoprotectant using low X-ray background micromesh mounts (Thorne et al 2003) and were able to observe single-crystal diffraction using the MD2 diffractometer at the X06SA beamline at the Swiss Light Source. Over 300 microcrystals purified from insect cells were tested to determine the atomic structure of CPV polyhedra to a resolution of 2 Å. To our knowledge, this is the first report of the atomic structure of functional intracellular crystals (Doye and Poon 2006).

The micron-sized polyhedra are the relevant biological assemblies and thus the polyhedron protein functions as a three-dimensional crystal, rather than as a single molecule or oligomer. A typical 2-micron crystal (FIG. 1*a*) has 200 body-centred cubic unit cells along each edge and contains approximately ten thousand virus particles. With a cell edge of 103 Å, the unit cells of polyhedra are far smaller than a 720 Å diameter icosahedral CPV particle. Electron microscopy revealed that virus particles are uniformly distributed in polyhedra and occupy holes in the lattice in place of at least 300 unit cells.

TABLE 1

Stability of polyhedra

| | Incubation Time | Diffraction |
|---|---|---|
| 8M Urea | 2 days | Yes |
| Detergents | | |
| 10% SDS | 2 days | Yes |
| Acids | | |
| 20% acetic acid, pH 1.9 | 2 days | Yes |
| 1M HCl | 2 days | No |
| Bases | | |
| 20 mM $NaH_2CO_3$, pH 10.5 | <1 min | Dissolved |
| 10 mM PBS, pH 11.0 | <1 min | Dissolved |
| Solvent | | |
| 100% Ethanol | 30 min | Yes |
| Physical stress | | |
| Dehydration* | 24 h | Yes |
| Freeze-Thaw | — | Yes |
| 90° C. | 16 h | No |

*Polyhedra in water were left to dry on a micromesh mount at relative humidity of 50% and frozen in liquid nitrogen without rehydration or cryoprotectant.

The atomic structures were determined for polyhedra with and without CPV particles and also for polyhedra where the virus particles were replaced by a protein kinase through fusion with the polyhedra-targeting sequence of the CPV turret protein. No significant difference was observed and the refined structures are essentially identical. These observations demonstrate that cargos of strikingly different molecular weights can be stably incorporated into polyhedra without disrupting the overall order of the crystalline lattice.

Structures of polyhedrins from infectious, recombinant and kinase-containing polyhedra have been deposited on 9 Jan. 2007 in the RCSB Protein Data Bank with accession codes 2OH5, 2OH6 and 2OH7.

Figure 1:
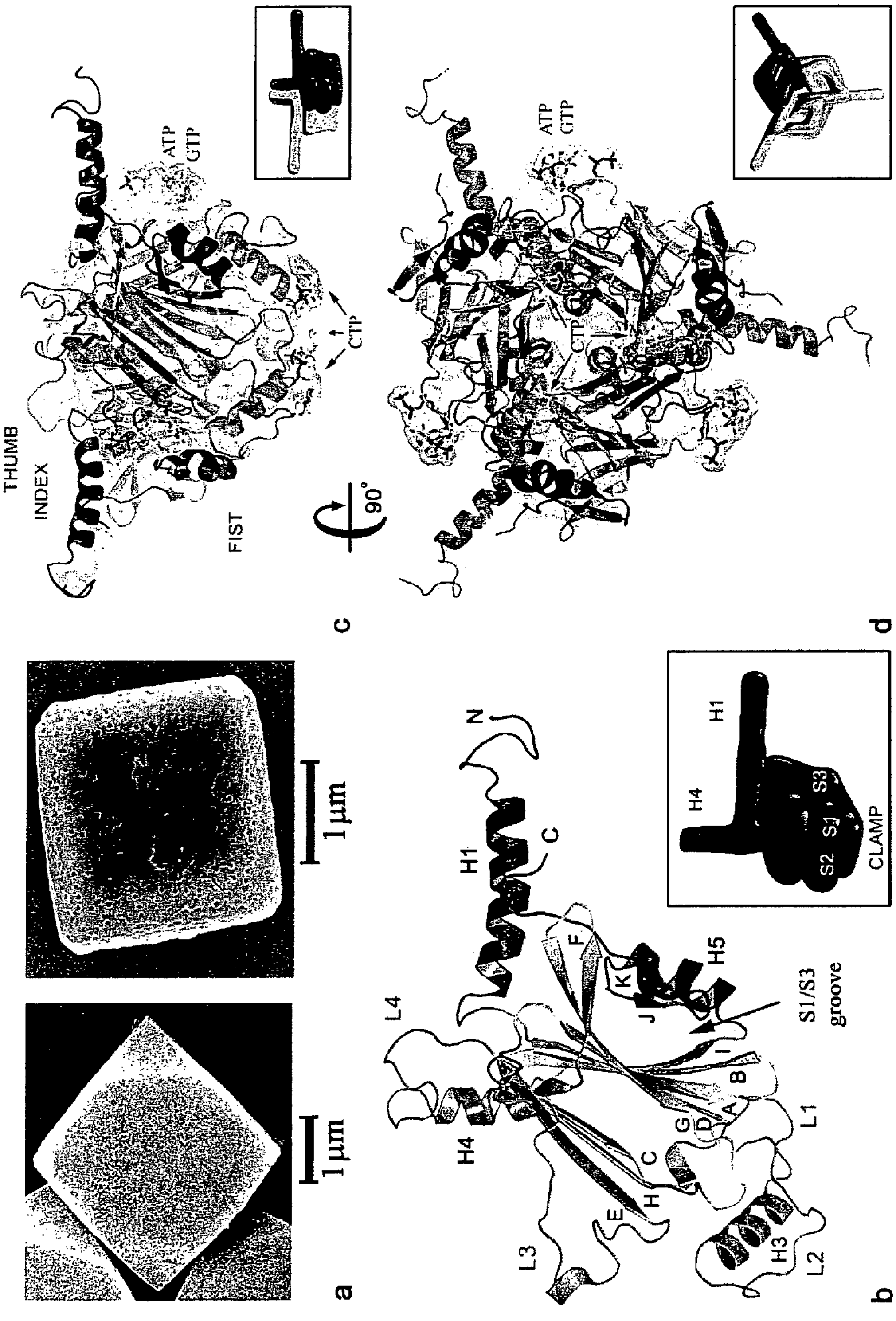
FIG. 1 Compact trimers are the building blocks of polyhedra.

Polyhedra are made from trimeric building blocks of the 28 kDa polyhedrin protein interlocked into a tight scaffold generated by the N-terminal α helix. The fold of polyhedrin has the shape of a left hand with the thumb and index finger outstretched. The finger is an N-terminal α helix (H1) which extends from the fist formed by a compact 3-layer β sandwich core. This sandwich is made up of two β sheets of six (S1) and three (S2) anti-parallel strands (FIG. 1*b*). The topology of the S1-S2 sandwich (IBADGF-CHE) is akin to the canonical jelly-roll found in many viral capsid proteins (BIDG-CHEF) although the exchange between strands A and I is novel. The third layer (S3) is formed by the C-terminal part of the protein and consists of a β hairpin preceded by a short α helix. S3 packs against the concave face of S1 forming a deep groove above S1 in the orientation shown in FIG. 1*b*. The central sandwich is flanked by additional helices with the H3 helix and adjacent loops forming a clamp-like protrusion above S1-S2 represented as the little finger in FIG. 1B. The thumb is an amphipathic helix (H4) located next to the 3-fold axis. The H1 helix, S1/S3 groove, clamp and H4 helix are all involved in the higher organization of polyhedra.

The polyhedrin trimers are composed of a central barrel in which the sandwich domains are held together by a bundle of H4 helices and the three clamps (FIG. 1*c-d*). They are formed mainly through hydrophobic interactions with over 25% (3800 Å2) of the total surface of a polyhedrin molecule buried in the trimer interfaces (FIG. 5). The trimers have 3-fold crystallographic symmetry so that one polyhedrin molecule constitutes the asymmetric unit of the crystal. Polyhedrin has a similar central β sandwich and overall trimeric shape to capsid proteins of double-stranded RNA viruses such as VP7 of bluetongue virus (Grimes et al 1995), Mu1 of reovirus (Liemann et al 2002) or VP2 of birnavirus (Coulibaly et al 2005). However, the quaternary arrangement in the trimer is different from these viral capsid proteins and polyhedrin trimers are organized into a 3-D body-centered cubic lattice, rather than an icosahedral shell.

The next level of organization in polyhedra is a tetrahedral cluster of four trimers at the centre of the I23 unit cell. All 12 polyhedrin molecules in this tetrahedral cluster are oriented with the thumbs pointing away from the centre of the cell and are linked together predominantly by interactions between the clamp regions (FIG. 2*a*). Two of these tetrahedral clusters constitute the unit cell of the crystal which is repeated a few hundred times along each axis to form micron-size cubic polyhedra. The tetrahedral clusters are tightly cross-linked in polyhedra essentially by non-covalent interactions mediated by the H1 helices (FIG. 2*b-c*). Firstly, H1 helices protruding from the tetrahedral clusters dock into the S1/S3 grooves of trimers of surrounding clusters (FIG. 2 finger-fist interactions). These are the most extended and intimate crystal contacts stabilizing polyhedra. Secondly, a bundle of H1 helices around crystallographic dyads further strengthens the crystal through long-range interactions between tetrahedral clusters (FIG. 2 finger-finger interactions).

The stability of polyhedra stems from an extensive network of interactions connecting the trimers and shielding over 70% of the polyhedrin surface from solvent. In polyhedra, each polyhedrin contacts eighteen other molecules, more than in any other protein crystal with the same I23 symmetry (the average is 7.7). Some of these interactions are comparable in their exquisite chemical and shape complementarity to antigen-antibody complexes Wodak et al 2002) (Surface Complementarity factor (Lawrence et al 1993) 0.70 for polyhedra and 0.64-0.68 for immune complexes). In particular, the H1 helix plays a central role in the architecture of polyhedra evident from the extent of crystal contacts that it mediates with three-quarters of its surface involved in intimate contacts with four neighbouring trimers (FIG. 5).

The dense packing of polyhedrin molecules also results in one of the lowest solvent contents reported for protein crystals (19%). It is interrupted only by narrow channels between unit cells, along and perpendicular to the crystallographic dyads, and by closed cavities around each lattice point, at the centre of the tetrahedral clusters (FIG. 3). The axial channels are narrow and blocked by H1 helices and the extensions of the cavity along the 3-fold axes of the crystal are blocked by H4 helices (FIG. 6). Polyhedra thus form a sealed matrix shielding embedded virus particles from the external environment. Polyhedra are exceptionally dense protein crystals with one of the lowest solvent content observed in the Protein Data Bank (19% including nucleotides, 22% for the protein only).

The tight packing of polyhedrin in the crystal leaves narrow channels and a central cavity. The central cavity is located at each lattice point and contains twelve CTP molecules. The cavity is lined by the clamp regions of 12 polyhedrin molecules. The outer diameter is 28.4 Å (distance Gly74-Gly74) and the inner diameter is 18.2 Å (distance His76-His76). His 76 is the only residue pointing inside the cavity and neighboring residues are all involved in the stabilizing the conformation of the loop 69-78.

Extensions of the cavity along crystallographic three-fold axis are blocked by helix H4 and in particular the residue Phe201. The smallest diameter (9 Å) of these extensions is defined by residues Tyr71 and Arg98-Asp96.

Interestingly, we found nucleotides at strategic places in both recombinant and infectious polyhedra. These nucleotides were determined to be ATP, GTP and CTP by mass spectrometry.

Stacked ATP and GTP molecules are bound at the interface between four tetrahedral clusters and a CTP molecule interacts with each of the twelve symmetry-related clamp regions lining the central cavity (FIG. 1*c-d*, 3*b* and FIG. 6). The specific interactions found at these two nucleotide binding sites near symmetry axes suggest that the nucleotides bind during crystallization and may play a role in nucleating the formation of polyhedra in the cytoplasm.

Once polyhedra are formed, the nucleotides are trapped in the crystal and were observed in crystals stored for three years in water.

These ligands have not been described previously and suggest that polyhedra can be modified to carry other small molecules such as drugs or fluorescent probes. Unlike existing virus-like nanoparticles (Douglas and Young 2006), these nanocontainers are easy to manipulate because of their size and strength, and they accommodate a wide range of cargos as shown here and in novel microarrays (Ikeda et al 2006) or promising bio-pesticides (Chang et al 2003).

Another attractive feature, of these nanocontainers is the possibility that the cargo can be released at alkaline pH. Despite their striking stability even at pH 2, polyhedra are primed for disassembly and dissolve readily above pH 10.5, releasing the virus particles in the alkaline midgut of larvae after ingestion. The difference in stability between low and high pH suggests that loss of hydrogen bonds and salt bridges is not sufficient to account for the dissolution of the crystals.

Instead, without wishing to be bound by theory, we propose a virus-release mechanism where deprotonation of a buried cluster of tyrosines (pKa~10.1) leads to partial unfolding of S3 and loss of the S1/S3 grooves, destabilizing the crystal because of their critical role in binding H1 helices (FIG. 4). We also propose that disruption of a network of salt bridges at high pH destabilizes the clamps by the introduction of unpaired buried charges and the loss of crucial inter-trimer and nucleotide-binding interactions (FIG. 4).

The polyhedrin forms unique intracellular crystals and has no close structural homologues. However the polyhedrin of a nucleopolyhedrovirus (NPV, Baculoviridae) assembles into a body-centered cubic lattice with similar dimensions as CPV polyhedra (Fujiwara et al 1984, Anduleit et al 2005). This protein is also predicted to have a long N-terminal helix comparable to the H1 helix which forms the scaffold of CPV polyhedra (Anduleit et al 2005). The architecture of polyhedra may therefore be shared by members of the Reoviridae and Baculoviridae families despite considerable evolutionary distance and fundamental differences in the life cycles of these viruses.

Cell culture systems are widely used in medicine, biomedical research and pharmacology and require specialized and costly media containing a variety of cell growth factors. These cell growth factors are cytokines, protein molecules necessary to simulate the growth and differentiation of cells in culture. Like most protein molecules, cytokines are comparatively unstable, so cell culture media must be frequently replenished. For this reason alternative long-lasting cell culture systems containing stably immobilized growth factors potentially have important applications. Stably immobilized growth factors can be considered to be useful for slow release of cytokines and for tissue engineering and regenerative medicine by using many stem cells including embryonic stem (ES) and induced pluripotent stem (iPS) cells.

In one embodiment, the present invention contemplates incorporation of a target molecule in a polyhedron for stable long-lasting release of the target molecule into a cell culture system. The skilled addressee would understand that the target molecule can comprise any molecule useful for eliciting a physiological response in a cell comprising but not limited to survival, growth, proliferation, phenotypic transformation, differentiation, or chemotaxis. The skilled addressee would also understand that a molecule that facilitates the expression of proteins from cells in culture systems can also be incorporated into a polyhedron and used in cell culture systems. These target molecules may comprise but are not limited to a polypeptide, a protein, a glycoprotein, a carbohydrate, a nucleotide, a nucleic acid, a lipid, a lipoprotein, a drug, a cytokine, an antigen, an antibody, an antibody fragment, a fluorescent molecule, a dye, a pH sensitive molecule a toxin, a venom and a bioactive molecule, a growth factor a chemokine or a mitogen.

The skilled addressee would understand that any type of cell culture system can be used comprising but not limited to any vessel adapted for culturing cells such as a cell culture plate, a roller bottle, a fermentation culture system and a bioreactor. It would also be clear to the skilled addressee that modified polyhedron comprising a target molecule can introduced into a cell culture system by a number of methodologies comprising but not limited to adding modified polyhedra containing a target molecule into culture medium or applying modified polyhedra containing a target molecule to a solid support surface which can be incorporated into a cell culture system for contact with a culture medium. This can include attachment of modified polyhedra to the bottom of a well of a tissue culture plate, or to a surface adapted for inclusion in any cell culture system such as a fermentation culture or bioreactor.

EXAMPLES

Example 1

Polyhedra Expression and Characterization

Expression and purification of recombinant and wild-type *Bombyx mori* CPV polyhedra in insect cells were carried as described elsewhere (Mori et al 1993). Polyhedra containing the human ZIP-kinase (Accession BAA24955) fused to an N-terminal fragment of the CPV turret protein were produced as previously described (Ikeda et al 2006). Scanning electron microscopy was performed on Pt coated samples. Mass spectrometry analyses confirmed the presence of ribonucleotide tri-phosphates in purified polyhedra and showed that acetylation of the N-terminal alanine is the only polyhedrin post-translational modification.

Example 2

Structure Determination

Crystals were spread on micromesh mounts (Thorne et al 2003) leaving a thin film of 50% ethylene glycol and data were collected at 120K on the MD2 diffractometer of the X06SA beamline (Swiss Light Source) with a strongly attenuated beam focused onto the crystal. Data were processed with Denzo/Scalepack (Otwinowski et al 1997) in space group I23 and datasets from 2-4 crystals were merged because of severe radiation damage. Successful heavy atom soaks were performed on recombinant polyhedra at high concentrations, usually half saturation in appropriate buffer. Heavy atom sites for four isomorphous derivatives including selenomethionine-substituted crystals were found by SHELX24 and refined at 2.6 Å using SHARP25. The structures of recombinant and infectious polyhedra and of polyhedra containing the ZIP-kinase were refined at resolutions of 2.1 Å, 1.98 Å and 2.45 Å respectively using Refmac526. The final models are essentially identical. The structure of infectious polyhedra is of high crystallographic quality for such small crystals (R=9.3%, Rfree=15.4% to 1.98 Å, Tables 2 & 3) and all residues lie in the allowed region of the Ramachandran plot (Lovell et al 2003).

TABLE 2

Data collection and refinement statistics (Molecular replacement)

| | infectious | Kinase-containing |
|---|---|---|
| Data collection | | |
| Cell dimensions | | |
| a = b = c (Å) | 102.78 | 102.74 |
| Resolution (Å) | 20-1.98 (2.05-1.98) | 20-2.45 (2.54-2.45) |

TABLE 2-continued

Data collection and refinement statistics (Molecular replacement)

| | infectious | Kinase-containing |
|---|---|---|
| $R_{sym}$ or $R_{merge}$ | 0.14 (0.50) | 0.13 (0.35) |
| I/σI | 13.9 (4.3) | 12.6 (3.7) |
| Completeness (%) | 99.0 (100) | 99.9 (99.4) |
| Redundancy | 7.2 (7.3) | 8.2 (3.5) |
| Refinement | | |
| Resolution (Å) | 18.76-1.98 | 18.8-2.45 |
| No. reflections | 11,348 | 6,092 |
| $R_{work}/R_{free}$ | 0.093/0.154 | 0.112/0.221 |
| No. atoms | | |
| Protein | 2056 | 2007 |
| Ligand/ion | 92/3 | 92/3 |
| Water | 286 | 137 |
| B-factors | | |
| Protein | 11.4 | 20.6 |
| Ligand/ion | 41.5/27.1 | 54.7/45.5 |
| Water | 26.3 | 21.5 |
| R.m.s deviations | | |
| Bond lengths (Å) | 0.013 | 0.016 |
| Bond angles (°) | 1.490 | 1.680 |

The space group for all datasets is I23. The number of crystals merged to obtain a complete dataset is indicated in parenthesis for the following datasets: infectious (3) and kinase-containing (5).

*Highest resolution shell is shown in parenthesis.

TABLE 3

Data collection, phasing and refinement statistics (recombinant polyhedra)

| | Native | KAuCN2 | KI/I2 | AgNO3 | Se-Met |
|---|---|---|---|---|---|
| Data collection | | | | | |
| Cell dimensions | | | | | |
| a = b = c (Å) | 102.96 | 103.11 | 102.36 | 102.92 | 103.00 |
| Resolution (Å) | 14.5-2.1 (2.17-2.10) | 18.8-2.8 (2.9-2.8) | 24.1-2.8 (2.9-2.8) | 24.3-2.6 (2.69-2.60) | 18.8-2.6 (2.69-2.6) |
| $R_{sym}$ or $R_{merge}$ | 0.13 (0.43) | 0.13 (0.26) | 0.13 (0.28) | 0.14 (0.30) | 0.15 (0.32) |
| I/σI | 7.6 (2.6) | 7.5 (4.0) | 12.7 (6.7) | 12.1 (4.7) | 13.1 (6.9) |
| Completeness (%) | 97.9 (98.2) | 96.9 (96.6) | 95.4 (98.2) | 98.7 (97.1) | 97.8 (99.6) |
| Redundancy | 3.6 (2.6) | 2.6 (2.6) | 5.8 (5.6) | 5.3 (3.4) | 7.3 (7.0) |
| Refinement | | | | | |
| Resolution (Å) | 14.5-2.1 | | | | |
| No. reflections | 9,434 | | | | |
| $R_{work}/R_{free}$ | 0.129/0.196 | | | | |
| No. atoms | | | | | |
| Protein | 2007 | | | | |
| Ligand/ion | 92/3 | | | | |
| Water | 141 | | | | |
| B-factors | | | | | |
| Protein | 17.3 | | | | |
| Ligand/ion | 56.6/42.3 | | | | |
| Water | 27.0 | | | | |
| R.m.s deviations | | | | | |
| Bond lengths (Å) | 0.012 | | | | |
| Bond angles (°) | 1.378 | | | | |

The space group for all datasets is I23. The number of crystals merged to obtain a complete dataset is indicated in parenthesis for the following datasets: Native (2), KAuCN2 (2), KI/I2 (3), AgNO3 (4) and Se-Met (2).

*Highest resolution shell is shown in parenthesis.

Example 3

Model Analysis and Illustrations

The oligomeric and crystal contact interfaces were characterized with AREAIMOL from CCP428 and the PISA29 server at the European Bioinformatics Institute. Solvent cavities and channels were analyzed with VOIDOO30 (Uppsala Software Factory). Illustrations were prepared with PyMOL v0.99 (DeLano Scientific, San Carlos, Calif., USA. http://www.pymol.org).

Example 4

H1-EGFP and polyhedrin were co-expressed and the fluorescence was observed by confocal microscopy (Z=0.7 um). Results are shown in FIG. 8.

Example 5

CPV polyhedra were produced using a baculovirus expression vector (Mori, H. et al. *J. Gen. Virol.* 74 (1), 99-102 (1993)) and then incubated with H1-EGFP suspension. One polyhedron was analysed and the fluorescence was detected from many spots on the surface (Z=0.7 um) Results shown in FIG. 9.

Example 6

H1-EGFP

An H1-EGFP fusion was designed to contain the N-terminal 30 amino acids of polyhedrin domain linked to an EGFP domain. To create H1-EGFP, a pEU-polyhedrin plasmid was amplified with the forward primer: SEQ ID NO. 1 and reverse primer: SEQ ID NO 2. The forward primer contained EcoRI site while reverse primer contained BamHI site. This resulting PCR fragment was digested with EcoRI-BamHI and ligated into the EcoRI-BamHI site of pEGFP-N3 (CLONTECH) to create pH1EGFP.

The H1EGFP construct was generated using the Gateway system (Invitrogen). These pEU-H76C and pH1EGFP plasmids were amplified by PCR using sets of primers, for H1EGFP: SEQ ID NO 3 and SEQ ID NO 4 containing an additional attB sequences for the BP recombination reaction. The amplified PCR fragment was introduced into plasmid vector pDONR221 (Invitrogen) via the BP recombination reaction, according to the recommendation of the manufacturer, to generate the entry clone pDNR-H1 EGFP. The construct was then used to perform an LR recombination reaction with the Gateway system compatible expression ("DEST") vector pDEST. We named the resultant vector pDEST-H1EGFP. The integrity of the constructs was confirmed by DNA sequencing (the PE Applied Biosystems Model 373A automated sequencer). The expression vector was co-transfected into Sf21 cells together with linearized AcNPV DNA (BaculoGold Baculovirus DNA, PharMingen). After incubation at 27° C. for 4 days, the culture medium was collected and centrifuged at 1000 g for 10 min, and the supernatant was used to infect more cells for amplification. Amplification of the recombinant virus was repeated three times, and a large amount of supernatant containing the recombinant baculovirus was obtained. The recombinant baculovirus obtained using pDEST-H1EGFP was designated AcH1EGFP. Sf21 cells ($5\times10^7$ cells per 75 $cm^2$ flask) were inoculated with the recombinant virus at a multiplicity of infection (MOI) of 10 PFU/cell. For double infections, each virus was added at an MOI of 5 PFU/cell. In this study, we carried out experiments: with H1EGFP and double infections of AcH1EGFP and AcCP-H which was produced polyhedrin into Sf21 cells. H1GFP-immobilized polyhedrin were isolated from the infected Sf21 cells and purified as described previously (Ikeda, 2006).

H1EGFP was purified from Sf21 cells 5 days after infection with H1EGFP recombinant baculovirus by ion-exchange chromatography. Briefly, to prepare the soluble extracts, the cells were collected by centrifugation and lysed by sonication in a PBS buffer. Protein purification was carried out by the following steps: (1) ion-exchange chromatography on DEAE Sepharose with NaCl gradient elution (0-0.2 M), and (2) gel filtration on Sephadex G-75. All chromatography was performed in 20 mM Tris buffer, pH 7.5, and the fraction containing H1EGFP were determined by the visible green fluorescence. The protein was dialyzed against 10 mM Tris (pH 7.0), and concentrated using centrifugal concentrators (Millipore, Centricon YM1000).

H1EGFP was crystallized using hanging-drop vapor diffusion method at room temperature by mixing 24, of H1EGFP with an equal volume of reservoir solution containing 1.5M ammonium sulfate and 15% glycerol and 100 mM Tris, pH 8.5. Small crystals allow to grow for about 3 days.

Sf21 cells were infected with two recombinant baculoviruses AcH1EGFP and AcCP-H.

Another polyhedra (VP3EGFP polyhedra) were also prepared by co-infection with AcVP3EGFP and AcCP-H. The polyhedra were recovered from the infected cells and purified as previously reported (Ikeda et al. (2001). The green fluorescence of H1 EGFP polyhedra was compared with that of VP3EGFP polyhedra. The results are shown in FIG. 10.

H1EGFP was expressed in Sf21 cells and purified by ion-exchange chromatography on DEAE Sepharose with NaCl gradient elution (0-0.2 M), and (2) gel filtration on Sephadex G-75. The purified H1EGFP was subjected to crystallization by using hanging-drop vapor diffusion method. Supplementary Information is linked to the online version of the Nature publication at www.nature.com/nature.

Example 7

H1/FGF-2

In this example stable CPV polyhedra containing the growth factor FGF-2 coupled with the H1 tag are shown to be active in stimulating growth in a cell culture assay using NIH 3T3 cells. Negative and positive control experiments were carried out to validate the experiment. The results are shown in FIG. 12.

A nucleotide sequence of N-terminal alpha helix (H1) of polyhedrin derived *Bombyx mori* CPV (BmCPV) SEQ ID NO 5 was cloned into NotI and EcoRI site of a baculovirus transfer vector pVL1392 using standard PCR and cloning techniques well known in the art to produce a plasmid designated pVL1392/H1. The nucleotide sequence of the H1 corresponds to an amino acid sequence shown in SEQ ID NO 6. GATEWAY cloning technology (Invitrogen) was used to facilitate the high throughput expression and immobilization of EGFP, FGF-2 and FGF-7. A destination vector (pDEST/N-H1) was constructed by inserting a reading frame cassette B (Invitrogen) into the XbaI site of pVL1392 (Invitrogen). The FGF-2 gene was amplified by PCR from the full-length human cDNA library, in which the attB1 and attB2 sequence was included in the primers. The resulting attB-flanked PCR products were cloned into a donor vector (pDONR221) by BP reactions of GATEWAY cloning technology using the BP clonase enzyme mixture. The ORFs were cloned between the attL1 and attL2 sites of the resulting entry vectors and were transferred to pDEST/H1 via LR clonase reactions with the LR clonase enzyme mixture. The resulting expression vector (pACH1) consisted of the N-terminal H1 sequence of BmCPV polyhedrin and foreign protein genes co-transfected into Sf21 cells with linearized AcNPV DNA (Baculogold Baculovirus DNA (Pharmingen)). In order to obtain foreign protein-immobilized polyhedra, the recombinant AcNPVs (AcH1/EGFP, AcH1/FGF-2, ACH1/FGF-7) were co-infected with AcCP-H which expressed BmCPV polyhedrin. The infected cells were collected, washed with phosphate-buffered saline (PBS; 20 mM $NaH_2PO_4$, 20 mM $Na_2HPO_4$, 150 mM NaCl, pH7.2) and homogenized to remove the cell membrane and nuclear envelope using the Ultrasonic Homogenizer VP-5S (TAITEC). The EGFP-polyhedra were purified by washing with sterile water. The FGF-2 polyhedra were then washed with sterile water containing penicillin (10,000 unit/10 and streptomycin (10 mg/ml) by centrifugation at 15,000 rpm for 10 min.

The FGF-2 was immobilized into the BmCPV polyhedra by using H1 sequence (H1/FGF-2 polyhedra). The biological activity of FGF-2 immobilized into the polyhedra was assayed as follows.

NIH3T3 cells were plated into a 96-well plate at a density of 4000 cells/well and cultured overnight in DME medium containing 10% fetal calf serum and then starved in alpha-MEM without fetal calf serum for 6 h, resulting in cessation of cell growth. The starved cells were then cultured in alpha-MEM containing either unmodified polyhedra, FGF-2 polyhedra ($0.1\times10^4$ to $1\times10^5$/4000 cells) or rFGF-2 (R & D systems) (0.1 ng to 100 ng) in the absence of fetal calf serum and for 4 days. Media containing rFGF-2 was replenished with fresh media containing rFGF-2 every two days.

The proliferation of the NIH3T3 cells was measured by the WST-8 assay as known in the art. Briefly, WST-8 is reduced by dehydrogenases present in cells to give a yellow colored product (formazan), which is soluble in the tissue culture medium. The amount of the formazan dye generated by the activity of dehydrogenases in cells is directly proportional to the number of living cells. For the WST-8 assay, Cell-Counting Kit-8 solution (Dojin Chemical Co., Ltd.) was added to the cultures and incubated for 4 h at 37° C. under 5% $CO_2$ in air, according to the manufacturer's instructions. Absorbance at 450 nm was determined using a microplate reader.

The H1/FGF-2 polyhedra stimulated the proliferation of the starved NIH3T3 cells in a dose dependent manner comparable with the proliferation detected in cells treated with rFGF-2. Specifically, proliferation of the NIH3T3 cells induced by the addition of $2\times10^4$ H1/FGF-2 polyhedra was very similar to that of cells treated with 10 ng rFGF-2. NIH3T3 cell growth was unaffected by treatment with unmodified polyhedra. The. These results are shown in FIG. 12.

Proliferation of the cells grown in medium containing H1/FGF-2 polyhedra was sustained in the absence of replenishing the H1/FGF-2 polyhedra. The proliferation was observed by only medium exchange without the addition of H1/FGF-2 polyheda. In contrast, proliferation of cells treated with medium containing rFGF-2 required feeding every 2 days with fresh medium containing rFGF-2.

Example 8

H1/FGF-7

In this example stable CPV polyhedra containing the growth factor FGF-7 coupled with the H1 tag are shown to be active in stimulating the growth of human epidermal keratinocytes in a cell culture assay. Negative and positive control experiments were carried out to validate the experiment. The results are shown in FIG. 13.

The FGF-7 was immobilized into the BmCPV polyhedra by using H1 sequence (H1/FGF-7 polyhedra) using the methods described in Example 7, above. The biological activity of FGF-7 immobilized into the polyhedra was assayed. H1/FGF-7 polyhedra ($0.2\times10^4$ to $1\times10^5$) and unmodified polyhedra were added to the surface of the wells of a 96-well plate and allowed to dry for 3 hr at room temperature.

Human Epidermal Keratinocytes (NHEK(F)) were purchased from KURABO. The frozen keratinocytes were washed with Defined Keratinocyte-SFM (GIBCO) and suspended in Keratinocyte-SFM The keratinocytes were plated into the wells of the 96 well plate pre-coated polyhedra as described above at a density of 2500 cell/cm$^2$ in Defined Keratinocyte-SFM in the absence of any growth supplement. As a positive control, the growth supplement including insulin, EGF, and FGF (GIBCO) was added to Defined Keratinocyte-SFM as indicated in FIG. 13.

Medium containing the growth supplement was replenished with fresh medium containing growth supplement every two days.

After 5 days incubation, the proliferation of keratinocytes was assayed. Cell-Counting Kit-8 solution (Dojin Chemical Co., Ltd.) was added to the cultures and incubated for 4 h at 37° C. under 5% $CO_2$ in air, according to the manufacturer's instructions. Absorbance at 450 nm was determined using a microplate reader.

The H1/FGF-7 polyhedra stimulated the proliferation of the keratinocyte in the absence of fetal calf serum and the growth supplement. The proliferation of the keratinocyte by the growth supplement was comparable with the addition of $5\times10^4$ H1/FGF-7 polyhedra. The shape of the keratinocyte proliferated by H1/FGF-7 polyhedra was very similar to that of the keratinocyte treated with growth supplement. These results are shown in FIG. 13.

Proliferation of the cells grown in medium containing FGF-7 polyhedra was sustained in the absence of replenishing the medium containing growth supplement. In contrast, proliferation of cells treated with medium containing growth supplement required feeding every 2 days with fresh medium containing growth supplement.

Although the invention has been described with reference to specific examples, it will be appreciated by those skilled in the art that the invention may be embodied in many other forms, in keeping with the broad principles and the spirit of the invention described herein.

Example 9

Thermanox coverslips were spotted with normal polyhedra, H1/FGF-2 polyhedra and rFGF-2 were spotted on the Thermanox coverslips. After complete desiccation, the coverslips were placed in 8-well plates, into which ATDC5 cells were seeded at a density of $1\times10^4$ cells per well. After 2 days incubation, the effects of these treatments on the proliferation of the cells were investigated. NP, normal polyhedral; F2P, spotted and desiccated H1/FGF-2 polyhedra; dF2, spotted and desiccated rFGF-2; F2, rFGF-2. Scale bar, 100 μm.

REFERENCES

1. Belloncik, S. & Mori, H. in *The INSECT VIRUSES* (eds Miller, L. K. and Ball, L. A.), 337-369 (Plenum Publishing Corporation, New York, 1998).

2. Miller, L. K. *The BACULOVIRUSES.* (Plenum Publishing Corporation, New York, 1997).
3. Summers, M. D. in *Adv. Virus Res.* (eds Bonning, B. C., Maramorosch, K., and Shatkin, A. J.), 68, 3-73 (Academic Press, New York, 2006).
4. Chang, J. H. et al. An improved baculovirus insecticide producing occlusion bodies that contain *Bacillus thuringiensis* insect toxin. *J. Invertebr. Pathol.* 84 (1), 30-37 (2003).
5. Glaser, R. W. & Chapman, J. W. The Nature of the Polyhedral Bodies found in Insect Cells. *Biol. Bull.* 30, 367-390 (1916).
6. Rohrmann, G. F. Polyhedrin structure. *J. Gen. Virol.* 67 (Pt 8), 1499-1513 (1986).
7. Riekel, C., Burghammer, M., & Schertler, G. Protein crystallography microdiffraction. *Curr. Opin. Struct. Biol.* 15 (5), 556-562 (2005).
8. Douglas, T. & Young, M. Viruses: Making Friends with Old Foes. *Science* 312 (5775), 873-875 (2006).
9. Ikeda, K. et al. Immobilization of diverse foreign proteins in viral polyhedra and potential application for protein microarrays. *Proteomics* 6 (1), 54-66 (2006).
10. Fields, B. N., Knipe, D. M., Howley, P. M., & Griffin, D. E. *Field's Virology.* (Lippincott Williams & Wilkins, Philadelphia, 2001).
11. Zhang, H. et al. Visualization of Protein-RNA Interactions in Cytoplasmic Polyhedrosis Virus. *J. Virol.* 73 (2), 1624-1629 (1999).
12. Hill, C. L. et al. The structure of a cypovirus and the functional organization of dsRNA viruses. *Nat. Struct. Mol. Biol.* 6 (6), 565-568 (1999).
13. Thorne, R. E., Stum, Z., Kmetko, J., O'Neill, K., & Gillilan, R. Microfabricated mounts for high-throughput macromolecular cryocrystallography. *J. Appl. Crystallogr.* 36 (6), 1455-1460 (2003).
14. Doye, J. P. K. & Poon, W. C. K. Protein Crystallization in vivo. *Curr. Opin. Colloid Interface Sci.* 11, 40-46 (2006).
15. Grimes, J., Basak, A. K., Roy, P., & Stuart, D. The crystal structure of bluetongue virus VP7. *Nature* 373, 167-170 (1995).
16. Liemann, S., Chandran, K., Baker, T. S., Nibert, M. L., & Harrison, S. C. Structure of the reovirus membrane-penetration protein, Mu1, in a complex with is protector protein, Sigma3. *Cell* 108 (2), 283-295 (2002).
17. Coulibaly, F. et al. The birnavirus crystal structure reveals structural relationships among icosahedral viruses. *Cell* 120 (6), 761-772 (2005).
18. Wodak, S. J. & Janin, J. Structural basis of macromolecular recognition. *Adv. Protein Chem.* 61, 9-73 (2002).
19. Lawrence, M. C. & Colman, P. M. Shape Complementarity at Protein/Protein Interfaces. *J. Mol. Biol.* 234 (4), 946-950 (1993).
20. Fujiwara, T. et al. Xray diffraction studies of the polyhedral inclusion bodies of nuclear and cytoplasmic polyhedrosis viruses. *Appl. Entomol. Zool.* 19, 402-403 (1984).
21. Anduleit, K. et al. Crystal lattice as biological phenotype for insect viruses. *Protein Sci.* 14 (10), 2741-2743 (2005).
22. Mori, H. et al. Expression of *Bombyx mori* cytoplasmic polyhedrosis virus polyhedrin in: cells by using a baculovirus expression vector, and its assembly into polyhedra. *J. Gen. Virol.* 74 (1), 99-102 (1993).
23. Otwinowski, Z. & Minor, W. in *Methods Enzymol.* (eds Carter, C. W. and Sweet, R. M.), 276, 307-326 (Academic Press, New York, 1997).
24. Schneider, T. R. & Sheldrick, G. M. Substructure solution with SHELXD. *Acta Cryst. D*58 (10 Part 2), 1772-1779 (2002).
25. de La Fortelle, E. & Bricogne, G. in *Methods Enzymol.* (eds Carter, C. W. and Sweet, R. M.), 276, 472-494 (Academic Press, New York, 1997).
26. Murshudov, G. N., Vagin, A. A., & Dodson, E. J. Refinement of Macromolecular Structures by the Maximum-Likelihood Method. *Acta Cryst. D* 53 (3), 240-255 (1997).
27. Lovell, S. C. et al. Structure validation by Calpha geometry: phi, psi and Cbeta deviation. *Proteins* 50 (3), 437-450 (2003).
28. Collaborative The CCP4 suite: programs for protein crystallography. *Acta Cryst. D* 50 (5), 760-763 (1994).
29. Krissinel, E. & Henrick, K. in *Lecture Notes in Computer Science* (eds Berthold, M. R.), 3695, 163-174 (Springer, Berlin Heidelberg, 2005).
30. Kleywegt, G. J. & Jones, T. A. Detection, delineation, measurement and display of cavities in macromolecular structures. *Acta Cryst. D* 50 (2), 178-185 (1994).
31. Ohmori, D. et al., *Biochim. Biophys. Acta,* 794, 15-21 (1984).
33. Sato, S., et al., *Biochim. Biophys. Acta,* 668, 277-289 (1981).
34. Drummond et al. *Nature Biotech.* 21:1192-1199 (2003)
35. Zhu et al. Curr. Opin. Chem. Biol. 7:55-63 (2003)
36. Wulfkuhle et al. Nature Rev. Cancer 3:267-275 (2003)
37. Tirumalai et al. Mol. Cell. Proteomics 2:1096-1103 (2003)
38. Ikeda et al. J. Virol. 75, 988-995 (2001)

The invention claimed is:

1. A method of preserving, prolonging or protecting the functionality of a target molecule, the method comprising the following steps:

(i) identifying a portion of a polyhedrin protein in a region of interest that contributes to the architecture of the cytoplasmic polyhedrosis virus polyhedron crystal structure, which region is identified using co-ordinates of a *Bombyx mori* cypovirus 1 polyhedron crystal structure;

(ii) attaching the target molecule to the portion of the polyhedron protein, thereby preparing a fusion molecule comprising the target molecule and at least the portion of the polyhedrin protein such that the fusion molecule is adapted for inclusion in a polyhedron crystal or part thereof; and (iii) including the fusion molecule in a polyhedron crystal or part thereof.

2. A method according to claim 1, wherein the region of interest comprises an N-terminus H1 helix of a polyhedrin protein or functional equivalent thereof.

3. A method according to claim 2, wherein the N-terminus H1 helix comprises SEQ ID No 6 or functional equivalent thereof.

4. A method of preparing a modified polyhedron or part thereof, the method comprising the steps of:

(a) identifying a portion of a polyhedrin protein in a region of interest that contributes to the architecture of the cytoplasmic polyhedrosis virus polyhedron crystal structure, which region is identified using co-ordinates of a *Bombyx mori* cypovirus 1 polyhedron crystal structure;

(b) preparing a fusion molecule comprising a target molecule and at least the portion of the polyhedrin protein such that the fusion molecule is adapted for inclusion in a polyhedron crystal or part thereof; and (c) incorporating the fusion molecule into a polyhedron by contacting the fusion molecule with a polyhedron, or co-expressing the fusion molecule with a polyhedron.

5. A modified polyhedron or part thereof prepared according to the method of claim 4, comprising:

the fusion molecule comprising the target molecule and at least the portion of a polyhedrin protein, wherein the portion of the polyhedrin protein comprise an N-terminal H1 helix of the polyhedrin protein or a functional equivalent thereof in the region of interest that contributes to the architecture of the cytoplasmic polyhedrosis virus polyhedron crystal structure, which region is identified using co-ordinates of a *Bombyx mori* cypovirus 1 polyhedron crystal structure, and wherein the fusion molecule is incorporated into a polyhedron by contacting the fusion molecule with a polyhedron, or co-expressing the fusion molecule with a polyhedron.

6. A complex comprising a polyhedron or part thereof and a fusion molecule, the fusion molecule comprising a target molecule and a polyhedrin protein or portion thereof, wherein the complex does not include an encapsulated virus particle, wherein the polyhedrin protein or portion thereof comprise an N-terminal H1 helix of the polyhedrin protein or a functional equivalent thereof in the region of interest that contributes to the architecture of the cytoplasmic polyhedrosis virus polyhedron crystal structure, which region is identified using co-ordinates of a *Bombyx mori* cypovirus 1 polyhedron crystal structure, and wherein the fusion molecule is incorporated into a polyhedron by contacting the fusion molecule with a polyhedron, or co-expressing the fusion molecule with a polyhedron.

7. A complex according to claim 6, wherein the polyhedron protein comprises SEQ ID No 6 or a functional equivalent thereof.

8. The modified polyhedron or part thereof according to claim 5, wherein the modified polyhedron or part thereof or the complex or part thereof is applied to a solid surface to produce an active surface and the functionality of the target molecule on the active surface is prolonged, protected or preserved.

9. The modified polyhedron or part thereof according to claim 8, wherein the modified polyhedron or part thereof or the complex or part thereof is desiccated on the active surface.

10. A method for culturing cells, comprising:

culturing cells in a medium which comprises a modified polyhedron or part thereof according to claim 5 or which is in contact with an active surface to which the modified polyhedron or part thereof is applied.

11. The method according to claim 10, wherein the target molecule or functional equivalent thereof is released from the active surface into the medium such that replenishment of the medium with the target molecule is not required.

12. The method according to claim 10, wherein the active surface is used in an assay.

13. The method according to claim 12, wherein the assay is a microarray assay.

14. The method according to claim 1 wherein the target molecule is selected from the group consisting of a polypeptide, a protein, a glycoprotein, a carbohydrate, a nucleotide, a nucleic acid, a lipid, a lipoprotein, a drug, a cytokine, an antigen, an antibody, an antibody fragment, a fluorescent molecule, a dye, a pH sensitive molecule a toxin, a venom, a bioactive molecule, a growth factor a chemokine and a mitogen.

15. A use The method according to claim 1, wherein the target molecule is a growth factor.

16. The method according to claim 15, wherein the growth factor is a fibroblast growth factor.

17. The method according to claim 16, wherein the fibroblast growth factor is fibroblast growth factor-2 or fibroblast growth factor-7.

* * * * *

UNITED STATES PATENT AND TRADEMARK OFFICE

CERTIFICATE OF CORRECTION

PATENT NO. : 8,554,493 B2
APPLICATION NO. : 12/529110
DATED : October 8, 2013
INVENTOR(S) : Metcalf et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 811 days.

Signed and Sealed this
Fifteenth Day of September, 2015

Michelle K. Lee
*Director of the United States Patent and Trademark Office*

SEQUENCE LISTING

```
<160> NUMBER OF SEQ ID NOS: 6

<210> SEQ ID NO 1
<211> LENGTH: 45
<212> TYPE: DNA
<213> ORGANISM: Artificial
<220> FEATURE:
<223> OTHER INFORMATION: primer

<400> SEQUENCE: 1

ccccgaattc atggcagacg tagcaggaac aagtaaccga gactt                    45


<210> SEQ ID NO 2
<211> LENGTH: 45
<212> TYPE: DNA
```

-continued

```
<213> ORGANISM: Artificial
<220> FEATURE:
<223> OTHER INFORMATION: primer

<400> SEQUENCE: 2

ccccggatcc agctgttgtt atagttgtat tgttcgctat tgaat                      45


<210> SEQ ID NO 3
<211> LENGTH: 51
<212> TYPE: DNA
<213> ORGANISM: Artificial
<220> FEATURE:
<223> OTHER INFORMATION: primer

<400> SEQUENCE: 3

ggggacaagt ttgtacaaaa aagcaggctt aatggcagac gtagcaggaa c               51


<210> SEQ ID NO 4
<211> LENGTH: 51
<212> TYPE: DNA
<213> ORGANISM: Artificial
<220> FEATURE:
<223> OTHER INFORMATION: primer

<400> SEQUENCE: 4

ggggaccact ttgtacaaga aagctgggta ttacttgtac agctcgtcca t               51


<210> SEQ ID NO 5
<211> LENGTH: 90
<212> TYPE: DNA
<213> ORGANISM: Bombyx mori

<400> SEQUENCE: 5

atggcagacg tagcaggaac aagtaaccga gactttcgcg gacgcgaaca aagactattc      60

aatagcgaac aatacaacta taacagcagc                                       90


<210> SEQ ID NO 6
<211> LENGTH: 28
<212> TYPE: PRT
<213> ORGANISM: Bombyx mori

<400> SEQUENCE: 6

Met Ala Asp Val Ala Gly Thr Ser Asn Arg Asp Phe Arg Gly Arg Glu
1               5                   10                  15

Gln Arg Asn Ser Glu Gln Tyr Asn Tyr Asn Ser Ser
            20                  25
```